US012746320B2

(12) United States Patent
MacLachlan et al.

(10) Patent No.: US 12,746,320 B2
(45) Date of Patent: Sep. 29, 2026

(54) MEDICAL WASTE COLLECTION SYSTEM FOR COLLECTING MEDICAL WASTE DURING A MEDICAL PROCEDURE

(71) Applicant: Stryker Corporation, Kalamazoo, MI (US)

(72) Inventors: Brian MacLachlan, Norton Shores, MI (US); Brooke Mason, Mattawan, MI (US); Kenneth Lee Soliva, Madison, WI (US); Colin Vincent Beney, Sun Prairie, WI (US); Sang Woo Nam, Middleton, WI (US)

(73) Assignee: Stryker Corporation, Portage, MI (US)

( * ) Notice: Subject to any disclaimer, the term of this patent is extended or adjusted under 35 U.S.C. 154(b) by 587 days.

(21) Appl. No.: 18/123,031

(22) Filed: Mar. 17, 2023

(65) Prior Publication Data

US 2023/0293802 A1 Sep. 21, 2023

Related U.S. Application Data

(60) Provisional application No. 63/321,238, filed on Mar. 18, 2022, provisional application No. 63/321,256, filed on Mar. 18, 2022.

(51) Int. Cl.
*A61M 1/00* (2006.01)

(52) U.S. Cl.
CPC ................ *A61M 1/60* (2021.05); *A61M 1/80* (2021.05); *A61M 2205/502* (2013.01)

(58) Field of Classification Search
CPC ...... A61M 2205/502; A61M 2205/583; A61M 2205/587; A61M 2205/50
See application file for complete search history.

(56) References Cited

U.S. PATENT DOCUMENTS 5,782,805 A * 7/1998 Meinzer ................. G16H 20/17 604/67
7,621,898 B2 11/2009 Lalomia et al.
(Continued)

FOREIGN PATENT DOCUMENTS

KR 20160115512 A 10/2016
WO 2007070570 A2 6/2007
(Continued)

OTHER PUBLICATIONS

English language abstract for KR 2016-0115512 A extracted from espacenet.com database on Mar. 22, 2023, 1 page.
U.S. Appl. No. 63/271,763, filed Oct. 26, 2021.

*Primary Examiner* — Ariana Zimbouski
*Assistant Examiner* — Matthew Wrubleski
(74) *Attorney, Agent, or Firm* — Howard & Howard Attorneys PLLC

(57) ABSTRACT

Methods for operating a medical waste collection system. The medical waste collection system includes a waste canister, a vacuum source, a user interface, and a controller. The controller operates the vacuum source so that an actual vacuum level does not exceed a suction limit set by the user through the user interface. A suction limit lock may be activated to permit the user to adjust the suction limit up to the suction limit lock and to prevent the user from adjusting the suction limit above the suction limit lock. If the user provides an input that indicates an attempt to adjust the suction limit above a selected vacuum level associated with the suction limit lock, then the user interface may display a prompt with an option to disable the suction limit lock.

14 Claims, 37 Drawing Sheets

(56) References Cited

U.S. PATENT DOCUMENTS

| | | | | |
|---|---|---|---|---|
| 10,105,470 | B2 | 10/2018 | Reasoner et al. | |
| 10,471,188 | B1 | 11/2019 | Zollinger et al. | |
| 11,160,909 | B2 | 11/2021 | Davie et al. | |
| 2001/0027791 | A1* | 10/2001 | Wallace | G06F 9/453 128/204.21 |
| 2005/0171495 | A1 | 8/2005 | Austin et al. | |
| 2009/0143734 | A1* | 6/2009 | Humayun | A61M 1/77 606/1 |
| 2013/0102980 | A1* | 4/2013 | Stubber | A61M 1/743 604/320 |
| 2014/0243766 | A1* | 8/2014 | Martuch | A61M 1/732 604/319 |
| 2014/0276531 | A1* | 9/2014 | Walsh | A61M 5/168 604/151 |
| 2014/0338529 | A1 | 11/2014 | Reasoner et al. | |
| 2015/0379237 | A1* | 12/2015 | Mills | G16H 20/17 |
| 2016/0331876 | A1* | 11/2016 | Smith | A61M 1/74 |
| 2021/0220528 | A1* | 7/2021 | Jalgaonkar | A61M 1/743 |
| 2021/0379525 | A1 | 12/2021 | Lalomia et al. | |
| 2022/0370706 | A1* | 11/2022 | Meganck | A61M 3/0216 |

FOREIGN PATENT DOCUMENTS

| | | | |
|---|---|---|---|
| WO | 2014066337 | A2 | 5/2014 |
| WO | 2017112684 | A1 | 6/2017 |
| WO | 2020210763 | A1 | 10/2020 |
| WO | 2022103912 | A1 | 5/2022 |

* cited by examiner

MEDICAL WASTE COLLECTION SYSTEM FOR COLLECTING MEDICAL WASTE DURING A MEDICAL PROCEDURE

CROSS-REFERENCE TO RELATED APPLICATIONS

This application claims priority to and all the benefits of U.S. Provisional Patent Application Nos. 63/321,238, filed on Mar. 18, 2022, and U.S. Provisional Patent Application No. 63/321,256, filed on Mar. 18, 2022, the entire contents of each being hereby incorporated by reference.

BACKGROUND

A byproduct of surgical procedures is medical waste that may be removed from the surgical site by a vacuum provided by a medical waste collection system. The medical waste may include liquids such as blood, interstitial fluid, mucus, irrigating fluid, and the like, and semisolid and solid bits of material entrained within the liquids. The medical waste is collected within a waste canisters supported on a chassis of the medical waste collection system.

Current and next generation implementations of the medical waste collection system include features that vastly exceed merely providing a vacuum. Additional features of the medical waste collection system include smoke evacuation, selectable vacuum levels, canister emptying and cleaning, among others, including those disclosed in commonly-owned U.S. Pat. No. 7,621,898, issued Nov. 24, 2009, the entire contents of which are hereby incorporated by reference, and sold under the tradename Neptune by Stryker Corporation (Kalamazoo, Mich.).

The waste canisters are typically disposed in housings and are often viewable through windows or openings in the housings. In some cases, a cover may be employed to shield the waste canisters from view. In such situations, it can be difficult to accommodate the cover with other components of the waste collection system in the housing. In some instances, operating the vacuum source at a high suction level may be undesirable for certain procedures such as pediatric procedures.

The medical waste collection system may include at least one user interface to present information and provide selectable options to the user. Yet advances in the scope and quantity of features being integrated into the medical waste collection system implicate a need in the art for commensurate development in the user interface and the methods for operating the medical waste collection system.

SUMMARY

A method of operating a medical waste collection system including a waste canister, a vacuum source, a user interface, and a controller according to a first aspect is disclosed. The method comprises the step of receiving, at the user interface, a first input from a user indicative of a suction limit. The method further comprises the step of controlling, with the controller, operation of the vacuum source such that an actual vacuum level generated by the vacuum source does not exceed the suction limit. The method also comprises the step of receiving, at the user interface, a second input from the user to activate a suction limit lock at a selected vacuum level. The method further comprises the step of permitting, with the controller, adjustment of the suction limit below the selected vacuum level, wherein the controller is configured to operate the vacuum source to adjust the actual vacuum level based on the adjustment of the suction limit. The method further comprises the step of preventing, with the controller, adjustment of the suction limit above the selected vacuum level associated with the suction limit lock.

A method of operating a medical waste collection system including a waste canister, a vacuum source, a user interface, and a controller according to a second aspect is disclosed. The method comprises the step of receiving, at the user interface, a first input from a user indicative of a suction limit. The method further comprises the step of controlling, with the controller, operation of the vacuum source such that an actual vacuum level generated by the vacuum source does not exceed the suction limit. The method also comprises the step of receiving, at the user interface, a second input from the user to activate a suction limit lock at a selected vacuum level. The method further comprises the step of permitting, with the controller, adjustment of the suction limit below the selected vacuum level, wherein the controller is configured to operate the vacuum source to adjust the actual vacuum level based on the adjustment of the suction limit. The method also comprises the step of receiving, at the user interface, a third input from the user indicative of an attempt to adjust the suction limit above the selected vacuum level associated with the suction limit lock. The method further comprises the step of displaying, on the user interface, a prompt with an option to disable the suction limit lock in response to the third input.

A method of operating a medical waste collection system including a waste canister, a vacuum source, a user interface, and a controller according to a third aspect is disclosed. The method comprises the step of receiving, at the user interface, a first input from a user indicative of a suction limit. The method further comprises the step of receiving, at the user interface, a second input from a user to activate an intermittent suction mode. The method also comprises the step of controlling, with the controller, operation of the vacuum source to provide intermittent suction in which the actual vacuum level generated by the vacuum source alternates between a non-zero vacuum level that is less than the suction limit, and zero vacuum level in which no suction is being drawn. The method further comprises the step of receiving, at the user interface, a third input from the user indicative of an attempt to adjust the suction limit. The method also comprises the step of displaying, on the user interface, a prompt with an option to disable the intermittent suction mode in response to the third input.

DETAILED DESCRIPTION

Figure 1:
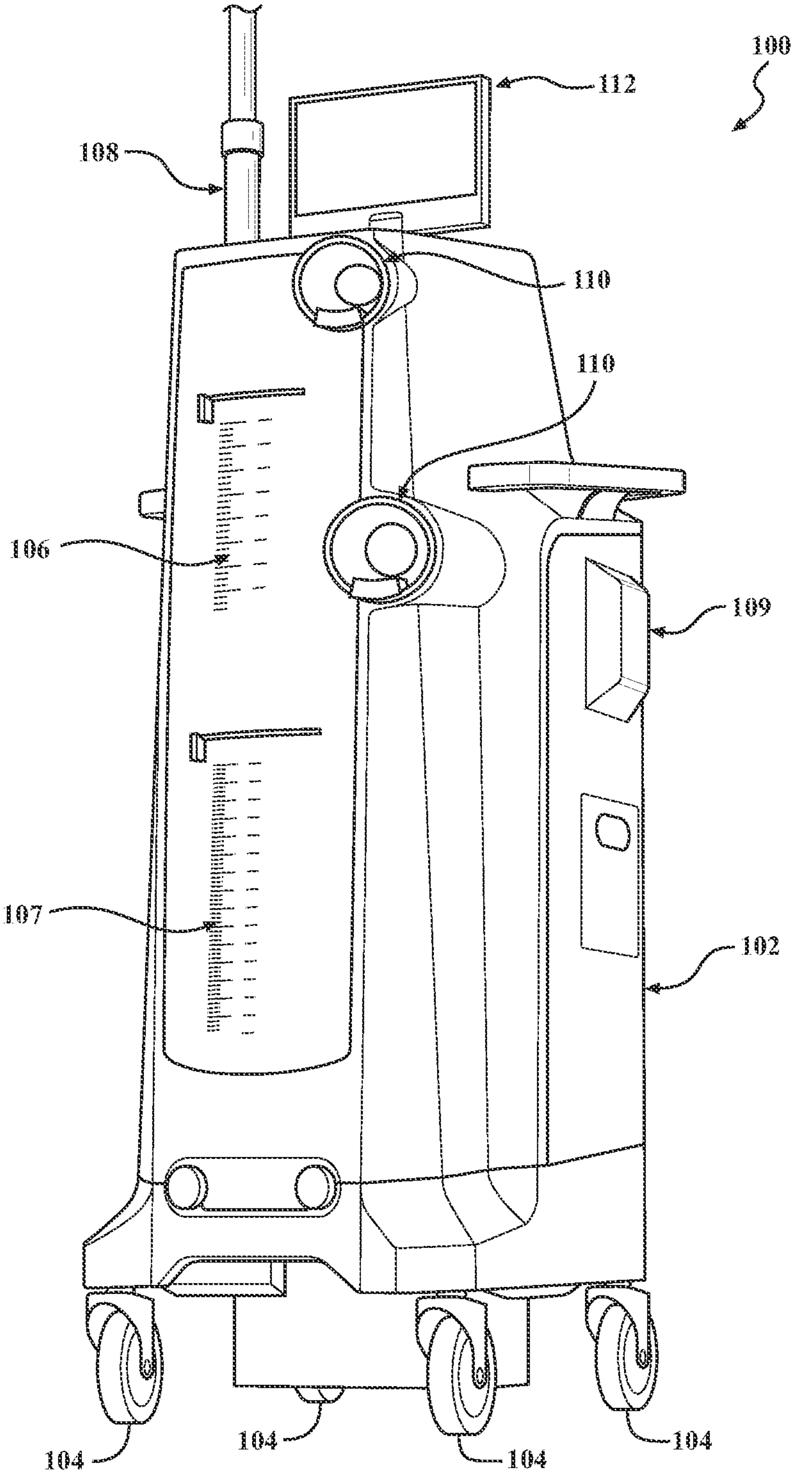
FIG. 1 is a front perspective view of a medical waste collection system in which a user interface is supported on a chassis.
Figure 2:
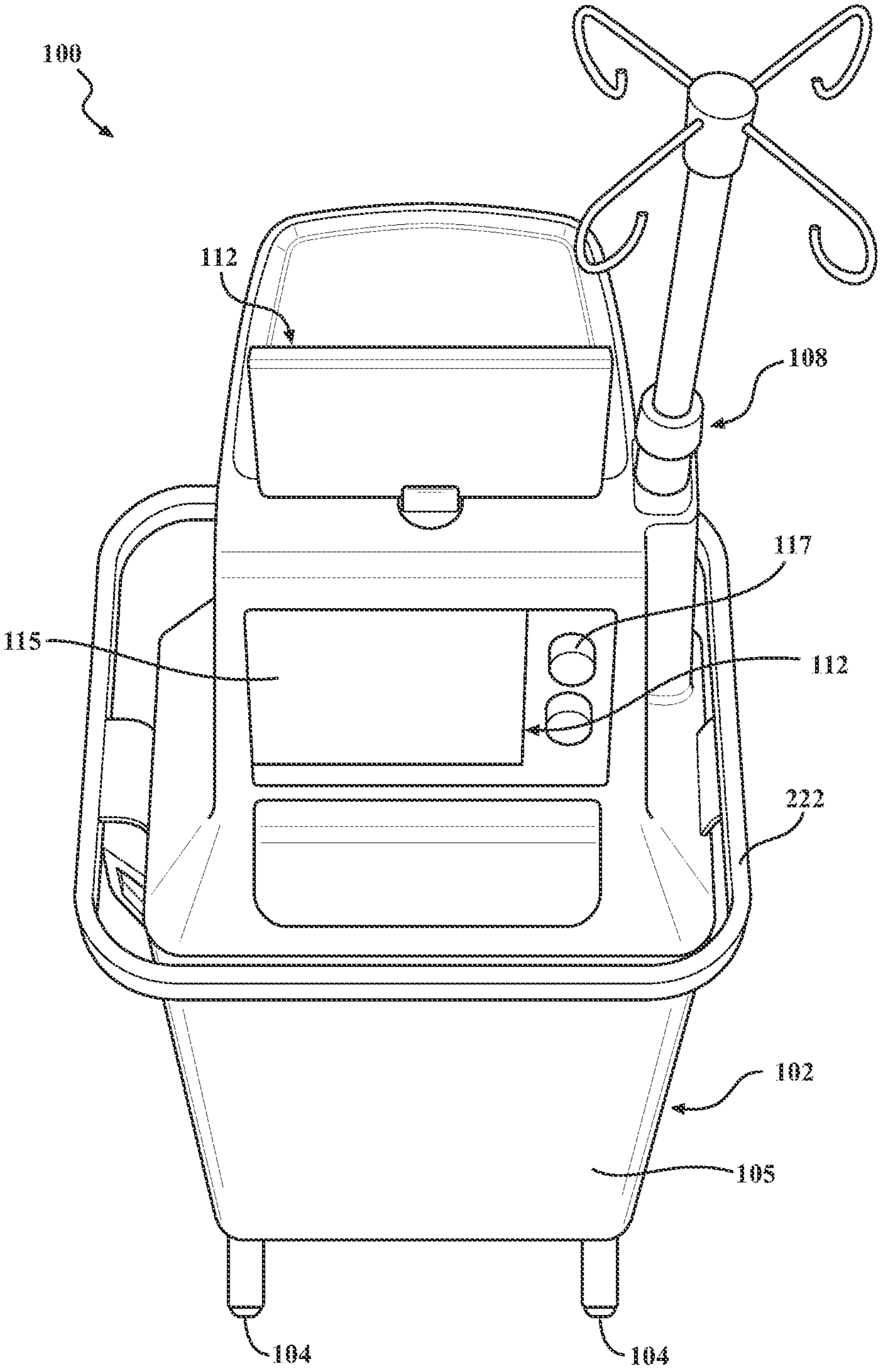
FIG. 2 is a top rear perspective view of the medical waste collection system of FIG. 1 in which another user interface is integrated into a rear of the chassis.

FIGS. 1 and 2 show a medical waste collection system 100 for collecting waste material generated during medical procedures. The waste material may include semisolid and solid material such as tissue, and liquid material such as blood, irrigating liquids, and other bodily fluids. The medical waste collection system 100 collects and stores the waste material until it is necessary or desired to empty and dispose of the waste material with a docking station. An exemplary docking station is disclosed in commonly-owned U.S. Pat. No. 7,621,898, issued Nov. 24, 2009, the entire contents of which are hereby incorporated by reference.

Figure 3:
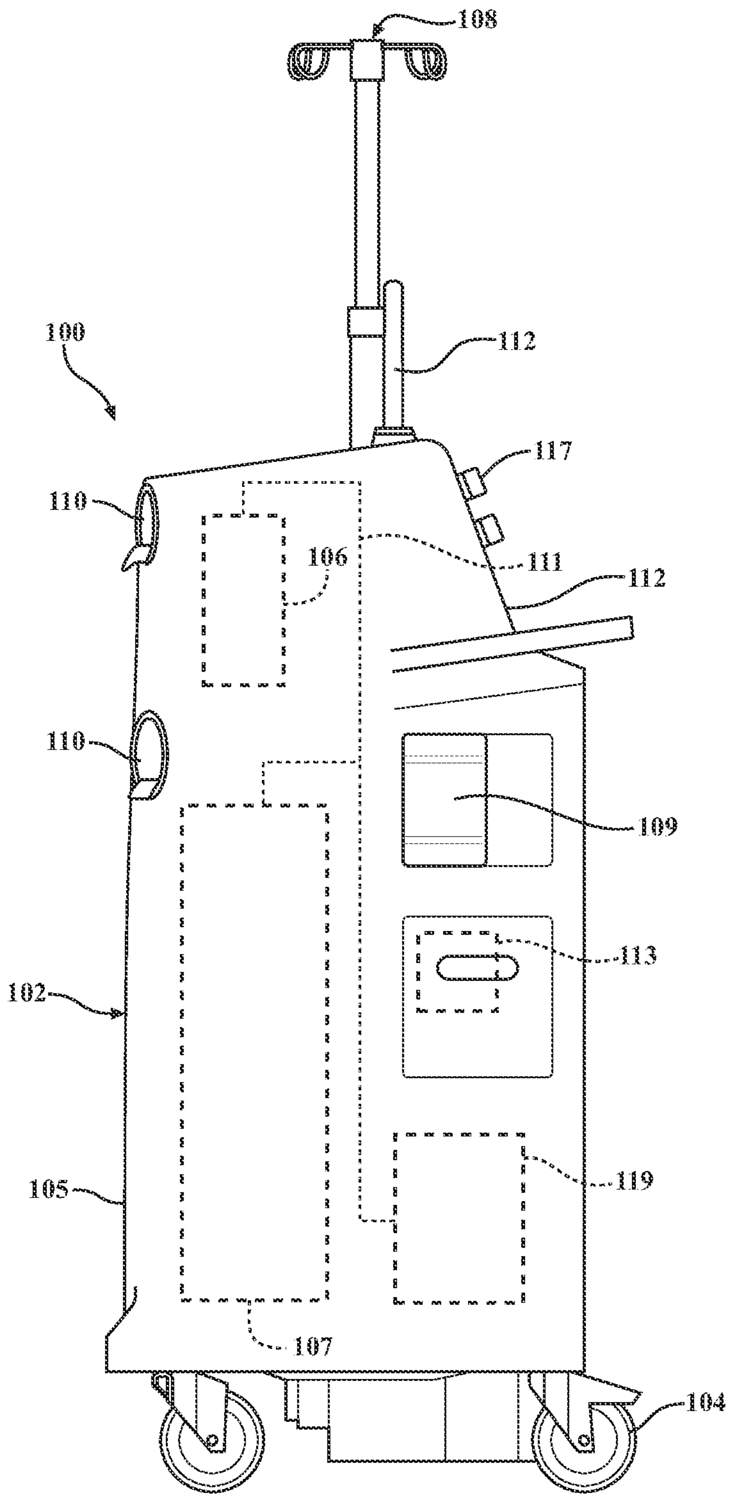
FIG. 3 is a schematic view of the medical waste collection system.

Several subsystems of the medical waste collection system 100 may be similar to those disclosed in the aforementioned U.S. Pat. No. 7,621,898, and in commonly-owned U.S. Pat. No. 10,105,470, issued Oct. 23, 2018, and U.S. Pat. No. 11,160,909, issued Nov. 2, 2021, the entire contents of each being hereby incorporated by reference. The medical waste collection system 100 may include a frame or chassis 102 and wheels 104 for moving the chassis 102 along a floor surface within a medical facility. The medical waste collection system 100 may also include a housing 105 defining an interior and described in further detail below. In some configurations, the chassis 102 may comprise the housing 105. In some configurations, the chassis 102 and the housing 105 may be integral. The medical waste collection system 100 includes an upper waste canister 106 defining a first waste volume for receiving and collecting the waste material, and a lower waste canister 107 defining a second waste volume for receiving and collecting the waste material. The lower waste canister 107 may be larger than the upper waste canister 106 and separated by an actuatable transfer valve in which the waste material from the upper waste canister 106 is emptied into the lower waste canister 107. The waste canisters 106, 107 may be disposed at least partially within the interior of the housing 105 and coupled to the chassis 102. It is contemplated that the waste canisters 106, 107 may assume any shape that is suitable for containing the waste material. The waste canisters 106, 107 may comprise multiple canisters as depicted in FIG. 3. In other configurations, a single canister may be employed.

An intravenous (IV) pole assembly 108, sometimes referred to as a support pole assembly, is coupled to the chassis 102 and includes a motor and/or actuator(s) to be selectively raised and lowered to a desired position, as described in greater detail further below. The medical waste collection system may further include, a fluid measuring subsystem (not identified) configured to measure a fluid level of the waste material within the waste canister, and a cleaning subsystem (not identified) in which rotatable sprayers direct pressurized liquid against an inner surface of each of the upper and lower waste canisters 106, 107. The docking station may provide water and detergent to be directed through the sprayers to clean the waste canister in one of multiple cleaning modes.

A vacuum source 119 may be supported by the chassis 102 or the housing 105 and configured to draw suction on the waste canisters 106, 107 through one or more vacuum lines 111 (shown schematically in FIG. 3). The vacuum source 119 may include a vacuum pump and/or a vacuum regulator configured to be in fluid communication with the waste canisters 106, 107. The vacuum regulator may be configured to regulate a level of the suction drawn by the vacuum pump on the waste canisters 106, 107. Suitable construction and operation of several subsystems of the medical waste collection system 100 are disclosed in commonly owned United States Patent Publication No. 2005/0171495, published Aug. 4, 2005, the aforementioned U.S. Pat. No. 7,621,898, International Publication No. WO 2020/210763, and the aforementioned U.S. Pat. No. 11,160,909, the entire contents of which are hereby incorporated by reference. In other configurations, the vacuum source 119 may be a separate unit that can be removably coupled to the medical waste collection system 100 to draw suction on the waste canisters. Suitable construction and operation of such a medical waste collection system is disclosed in the aforementioned U.S. Pat. No. 10,105,470.

The medical waste collection system 100 includes at least one receiver 110 supported on the chassis 102. The receivers 110 each define an opening sized to removably receive at least a portion of a manifold. A suction path may be established from suction tubes to one of the upper and lower waste canisters 106, 107 through the manifold removably inserted into a respective one of the receivers 110. Exemplary implementations of the receiver and the manifold are disclosed in commonly-owned U.S. Pat. No. 10,471,188, issued Nov. 12, 2019, the entire contents of which are hereby incorporated by reference. The receivers 110 may be further configured to removably receive at least a portion of a device or cartridge for quantifying blood loss. Alternatively, a separate interface may be disposed on the chassis 102 and configured to receive the cartridge. Exemplary implementations of the cartridge are disclosed in commonly-owned International Publication No. 2022/103912, published on May 19, 2022, the entire contents of which are hereby incorporated by reference.

The medical waste collection system 100 may comprise a controller 113 (shown schematically in FIG. 3). The controller 113 may comprise a plurality of sub-controllers, each including one or more microprocessors, processors, systems on a chip, etc. to operate certain features of the medical waste collection system 100. The sub-controllers may communicate with the controller 113 along a communications bus or by other conventional methods. An on-board user interface 112, realized as a control panel and described in greater detail further detail below is configured to generate signals to and receive signals from the controller 113 to permit a user to selectively operate the vacuum source 119 and other systems of the medical waste collection system 100. In one configuration, the controller 113 is configured to generate signals to the vacuum source 119 to operate the vacuum regulator to adjust the vacuum level in one or more of the waste canisters 106, 107. Suitable operation of a medical waste collection system 100 to control vacuum levels in the waste canisters 106, 107 is disclosed in the aforementioned U.S. Pat. No. 7,621,898, the entire contents of which are hereby incorporated by reference.

In the configuration illustrated in FIG. 2, a second user interface realized as a docking control panel 115 has a display facing the opposite direction to the first user interface 112. The docking control panel 115 may display to the user a number of different indications relating to docking and cleaning procedures such as selection of a wash mode, abortion of a wash mode, whether the waste canister has been emptied of waste material, the duration remaining before a wash mode will finish, release of the medical waste collection system 100 from the docking station, error notifications, etc. It is contemplated that the arrangement and function of the first and second user interfaces may be switched.

As noted above, the user interface 112 may be supported on the chassis 102 and/or the housing 105. FIG. 1 shows a user interface 112 supported atop and oriented towards a front of the chassis 102, and FIG. 2 shows another user interface 112 integrated within and oriented towards a rear of the chassis 102. The user interface 112 may be disposed on a swivel to provide for selectively moving the user interface 112 to a desired viewing position. The information, selectable options, and selectable controls displayed on the user interfaces 112 may the same or different, or selectable to be the same or different based on preferences of the user.

FIGS. 4-26 illustrate exemplary configurations of the user interface 112 at several points in operation of the medical waste collection system 100. In general, the user interface 112 includes a display configured to output the information, the selectable options, the selectable controls in an intuitive manner to facilitate ease of use and seamless workflow between the various functions of the medical waste collection system 100 to be described. The display may be a touchscreen display, and/or the user interface 112 may include inputs such as knobs 117 such as shown adjacent the display in FIG. 2.

Figure 4:
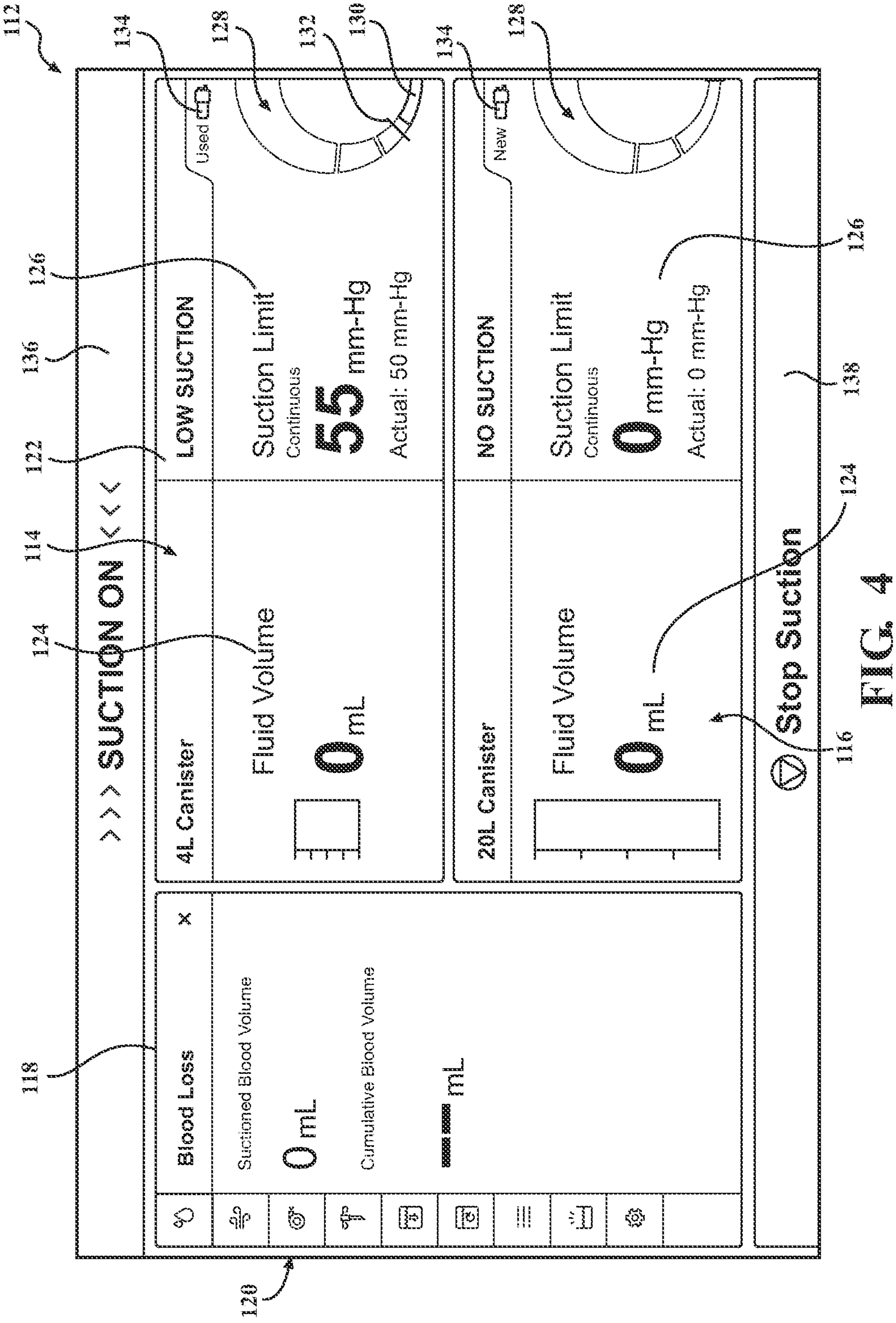
FIG. 4 illustrates a first exemplary configuration of a user interface for the medical waste collection system.

Referring to FIG. 4, the user interface 112 includes a first canister tile 114, a second canister tile 116, a working tile 118, and a toolbar 120. The first canister tile 114 is configured to display information relevant to operation of the upper waste canister 106, and the second canister tile 116 is configured to display information relevant to operation of the lower waste canister 107. A tile header 122 may be suitably arranged within each of the first and second canisters tiles 114, 116 to textually identify a corresponding one of the upper and lower waste canisters 106, 107 and provide alerts to be described. As noted above, it is contemplated that the medical waste collection system 100 may include a single waste canister in which case the user interface 112 may include a singular canister tile. The figures show the toolbar 120 oriented vertically along a left side of the user interface 112, but other suitable locations include the upper, lower, and right sides. The toolbar 120 includes a series of icons each corresponding to one of the functions (or submenus) of the medical waste collection system 100 to be described. The toolbar 120 may not include text so as to limit its footprint on the display.

Each of the first canister tile 114 and the second canister tile 116 includes a volume field 124, a suction field 126, and a vacuum meter 128. As implied by its name, the volume field 124 is configured to display information indicative of a waste volume of the waste material within the upper and lower waste canisters 106, 107. The figures show the volume field 124 including a graphical representation of the canisters and a numerical value with a unit of measurement. The suction field 126 is configured to display information indicative of vacuum levels on the upper and lower waste canisters 106, 107. The information may include an actual vacuum level, a suction limit, and a suction mode. The vacuum meter 128 may be a graphical counterpart to the numerical values provided in the suction field 126. The vacuum meter 128 is configured to display and convey several metrics indicative of the operation of the medical waste collection system, including the actual vacuum level, the suction limit, and a suction limit lock to be described. In one implementation, the vacuum meter 128 is arranged as a semicircular arc positioned on a right side of the first and second canister tiles 114, 116. The semicircular arc has a narrower lower aspect and a wider upper aspect generally representing the corresponding increase in the vacuum levels when displayed on the vacuum meter 128. Further, the semicircular arc may be divided into sectors each corresponding to one of multiple vacuum categories such as a low suction, medium suction, and high suction. Each sector may be configured to be displayed on the vacuum meter 128 in a different color. For example, low suction may be green, medium suction may be yellow, and high suction may be orange. The color-coding and the widening about the arc cooperate to display the information in an intuitive manner that can be readily appreciated by the user, particular to draw added attention when the medical waste collection system 100 is operated at higher vacuum levels at which more care may need to be exercised.

A vacuum indicia 130 is superimposed on the vacuum meter 128 to correspond to the actual level of vacuum. The presentation of the vacuum indicia 130 corresponds to the numerical value displayed on the suction field 126. For example, a proportion of the vacuum meter 128 that is superimposed by color of the vacuum indicia 130 corresponds to a proportion of the maximum level achievable by the medical waste collection system 100. The medical waste collection system 100 may be operable to a maximum of 530 millimeters of Mercury (mmHg), and thus a position of the vacuum indicia 130 on the vacuum meter 128 may a proportion of the 530 mmHg. The proportion may or may not be a linear relationship.

Figure 5:
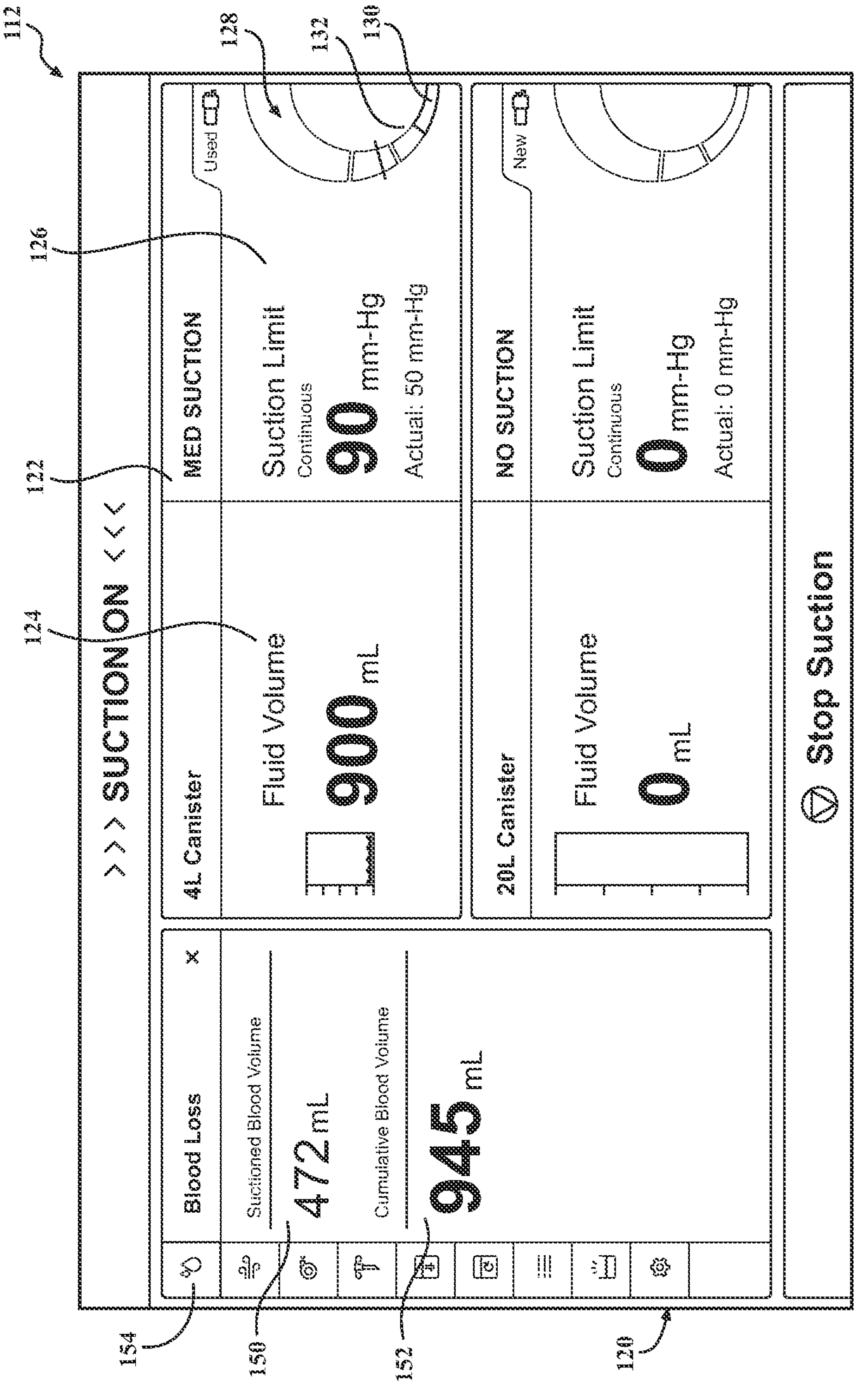
FIG. 5 illustrates a second exemplary configuration of the user interface for the medical waste collection system.
Figure 6:
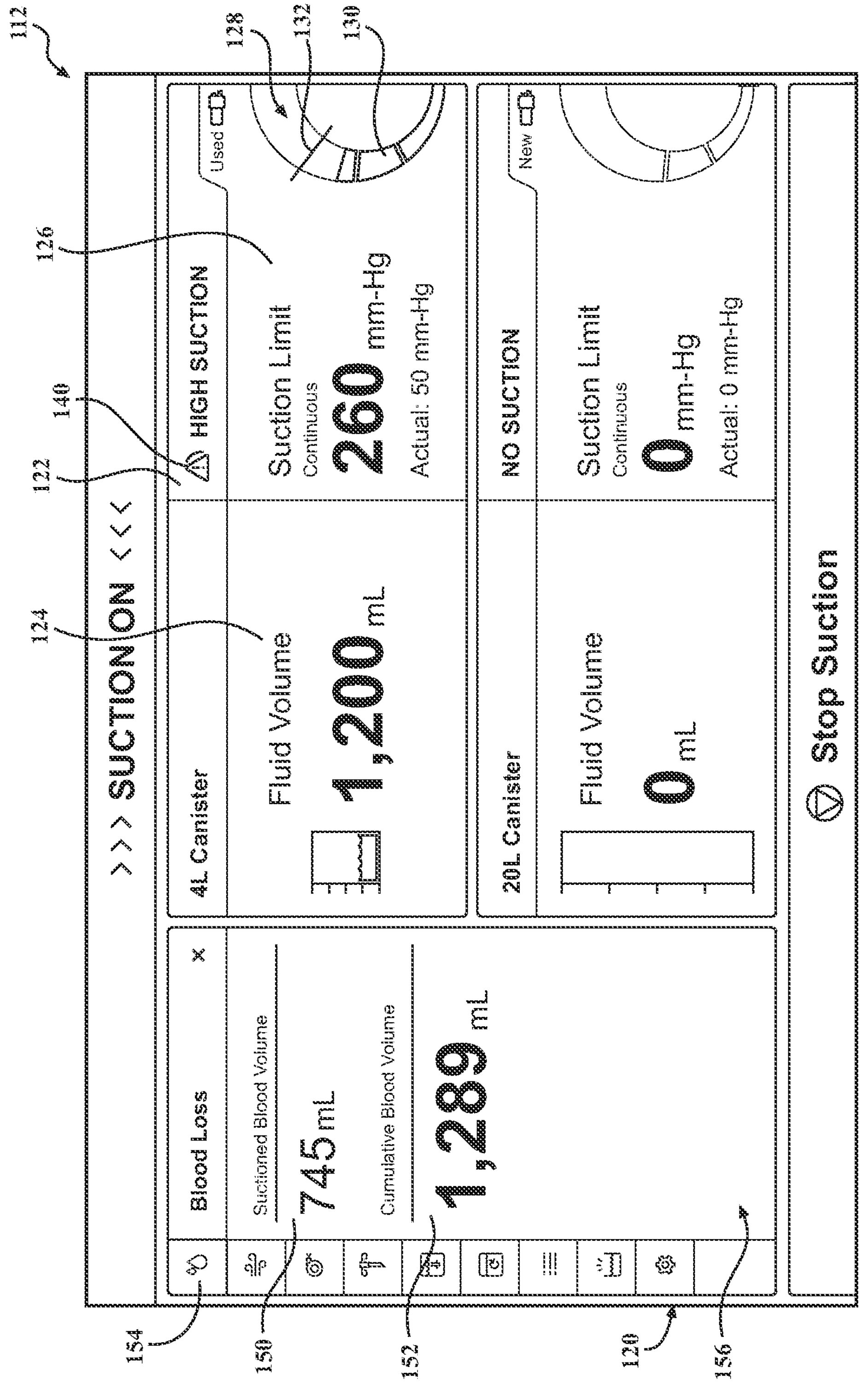
FIG. 6 illustrates a third exemplary configuration of the user interface for the medical waste collection system.

A suction limit indicia 132 may also be superimposed on the vacuum meter 128. The suction limit indicia 132 may be a graphical counterpart to the numerical value of the suction limit provided in the suction field 126. The suction limit indicia 132 may be represented by a hash or tick mark superimposed at the appropriate position along the semicircular arc of the vacuum meter 128. The suction limit indicia 132 may be colored to correspond to one of the sectors within which the suction limit is set. For example, FIG. 4 shows the suction limit set at 55 mmHg, corresponding to low suction, and therefore the suction limit indicia 132 may be colored as green. FIGS. 5 and 6, by contrast, show the suction limits set at values corresponding to medium suction and high suction, respectively, and therefore the suction limit indicia 132 may be colored as yellow and orange, respectively.

The tile header 122 may include textual and/or graphical information regarding the actual vacuum level. The textual information may include "low suction," "medium suction," or "high suction" corresponding to the vacuum category based on the selected suction limit or the actual vacuum level. The textual information may be contained within a background that is colored to corresponding to the vacuum category. In particular, the color coding of the tile header 122 is the same as the color coding of the vacuum indicia 130. Therefore, the user may be able to readily ascertain the vacuum category, the actual vacuum level, and the suction limit from multiple locations on the user interface 112.

Each of the first canister tile 114 and the second canister tile 116 may include a manifold indicia 134 configured to provide information as to a status of the manifold received within the receiver 110. It is known that the manifold may be a single-use component, and therefore it is desirable to show whether the manifold is being or has been used such that will need to be removed and replaced. The manifold indicia 134 may include textual and graphical information. For example, the manifold indicia 134 of the first canister tile 114 shows the manifold as "used" with the graphical representation of the manifold being magenta in color, whereas the manifold indicia 134 of the second canister tile 116 shows the manifold as "new" with the graphical representation of the manifold being white in color. The manifold indicia 134 may also indicate whether no manifold has been inserted into the receiver 110 (see FIGS. 9 and 10).

The user interface 112 may include a vacuum status bar 136 and a vacuum control bar 138. The vacuum status bar 136 is configured to display whether the medical waste collection system 100 is operating, and the vacuum control bar 138 is configured to be selected by the user to start or stop operation of the medical waste collection system 100. The vacuum status bar 136 may include textual and graphical information. The vacuum status bar 136 of FIG. 4 may include the text "suction on" overlaid on a green background to indicate the medical waste collection system 100 is active. The vacuum control bar 138 may include the text "stop suction" overlaid on a red background to indicate the medical waste collection system 100 would "stop" of selected. The backgrounds of the vacuum status bar 136 and the vacuum control bar 138 may change color with the medical waste collection system 100 being inactive.

The user interface 112 at points of operation of the medical waste collection system 100 is described with reference to FIGS. 4-9. FIG. 4 shows the vacuum source operating with a manifold received within the receiver 110 of the upper waste canister 106. The suction limit is set at 55 mmHg and the actual vacuum level being is 45 mmHg. The controller 113 of the medical waste collection system 100 may operate the vacuum source in a continuous or intermittent manner to maintain the actual vacuum level, which may fluctuate about the actual vacuum level. The user may increase the actual vacuum level up to the suction limit. Further attempt to increase the actual vacuum level above the suction limit may not be realized by the controller 113. The suction limit may itself be increased or decreased through input to the user interface 112. FIG. 4 shows that there is no waste material yet collected in the upper waste canister 106—e.g., the surgical procedure has just commenced.

The user may provide the input to the user interface 112 to increase the suction limit. FIG. 5 shows the suction limit indicia 132 superimposed upwardly along the vacuum meter 128 and corresponding to the vacuum category of medium suction. The tile header 122 also includes the text of "medium suction," which may be overlaid on a yellow background, and the suction field 126 numerically shows the value of the suction limit. Even without necessarily appreciating the numerical value of the suction limit, the user may quickly ascertain that the medical waste collection system 100 is set to be operated at a medium suction level, and decide whether the medium suction category is appropriate and adjust if needed. At this particular moment, the actual vacuum level remains at 45 mmHg as reflected in the suction field 126 and the vacuum meter 128. In other words, the user may have increased the suction limit, but not yet increased the actual vacuum level. The volume field 124 indicates that 900 milliliters (mL) of waste material has been collected in the upper waste canister 106.

The user may provide another input to the user interface 112 to further increase the suction limit. FIG. 6 shows the suction limit indicia 132 superimposed further upwardly along the vacuum meter 128 and orange in color corresponding to the vacuum category of high suction. The tile header 122 also includes the text of "high suction" overlaid on an orange background, and the suction field 126 numerically shows the value of the suction limit. Further, the tile header 122 also includes a warning icon 140 positioned adjacent the text. Since the suction limit (and the actual vacuum level) is in the high suction category, the warning icon 140 is to remind users to exercise case should the actual vacuum level also enter the high suction category, as is the case in FIG. 6. Moreover, the sectors of the vacuum meter 128 are correspondingly color coded to the tile header 122, or vice versa, in which the sectors are colored in accordingly as the actual vacuum level increases. The volume field 124 indicates that 1200 mL of waste material has been collected in the upper waste canister 106. The graphical representation of the waste canister in the volume field 124 has altered to show a liquid represented therein in proportion to a capacity of the upper waste canister 106 that has been filled with the waste material.

Figure 7:
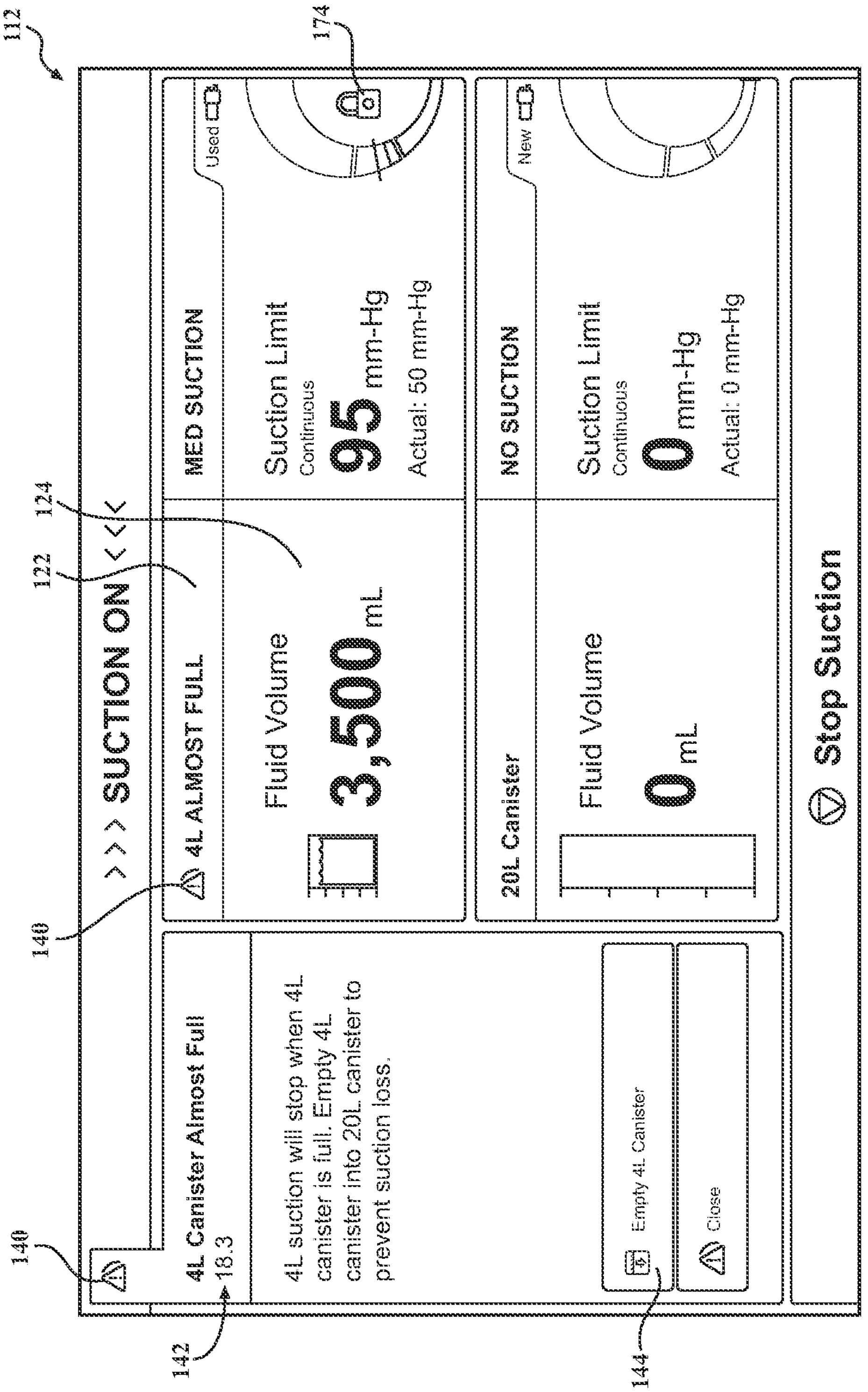
FIG. 7 illustrates a fourth exemplary configuration of the user interface for the medical waste collection system.
Figure 8:
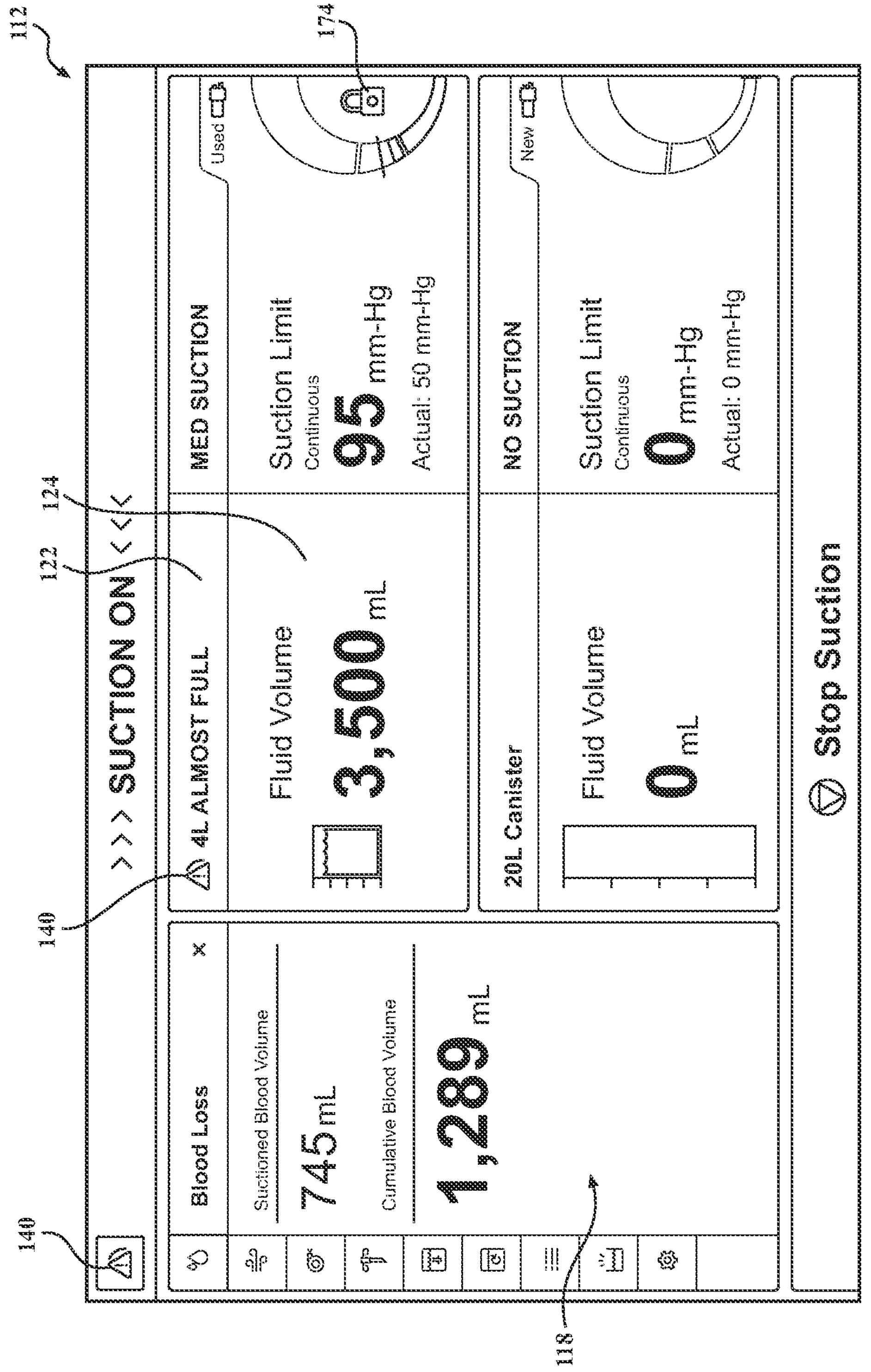
FIG. 8 illustrates a fifth exemplary configuration of the user interface for the medical waste collection system.
Figure 9:
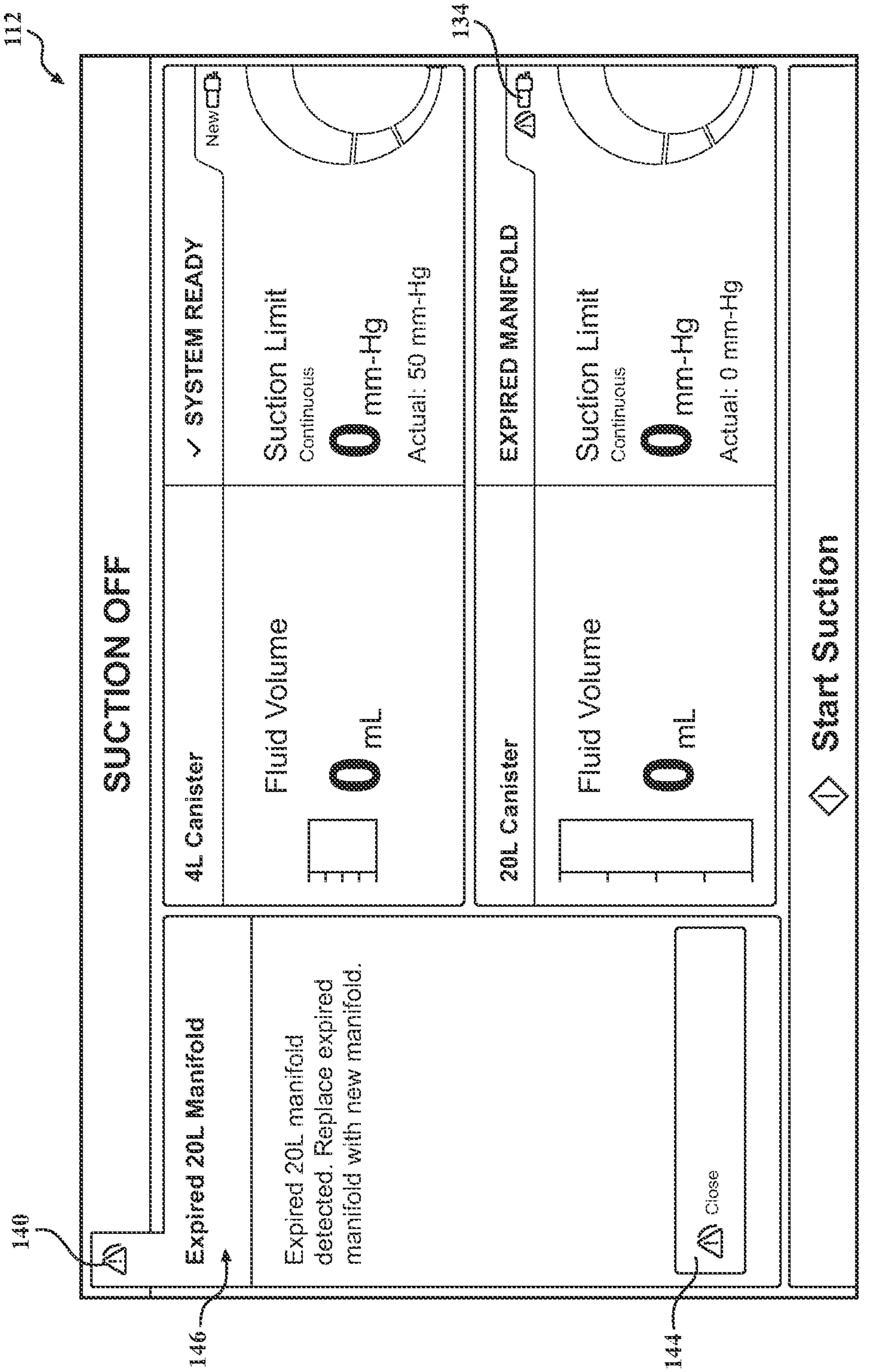
FIG. 9 illustrates a sixth exemplary configuration of the user interface for the medical waste collection system.

At some point, the upper waste canister 106 (or the lower waste canister 107) may become nearly full as sensed by the fluid measuring subsystem. The user interface 112 is configured to provide several alerts. First, the graphical representation of the waste canister in the volume field 124 is shown as nearly full, and the color of the graphical representation has been changed. Second, the tile header 122 includes textual and graphical information. The tile header 122 includes text indicating that the upper waste canister 106 is "nearly full," and the color may be changed to correspond to the color of the graphical representation of the waste canister in the volume field 124. Third, the tile header 122 may include a warning icon 140. Fourth, the working tile 118, which previously may have been displaying a status of one of the functions of the medical waste collection system 100, is updated with a canister volume alert 142. A header of the canister volume alert 142 itself may include textual and graphical information, the latter may again include a color corresponding to the color of the graphical representation of the waste canister in the volume field 124 as well as the color of the tile header 122. Therefore, the user may quickly ascertain that these informational items correspond to one another and take remedial action as needed. The canister volume alert 142 may include selectable options 144, including emptying the upper waste canister 106 into the lower waste canister 107 (see also FIG. 17), or minimizing the canister volume alert 142 within the working tile 118. FIG. 8 is indicative of the user selecting the selectable option 144 to close the canister volume alert 142 (from FIG. 7), in which case the working tile 118 returns to displaying the status of one of the subsystems. The warning icon 140, however, remains present and color coded in the corresponding manner for the user later address as necessary. The warning icon 140 is selectable to maximize the canister volume alert 142 within the working tile 118. FIG. 9 shows the user interface 112 providing a manifold alert 146 if the manifold is expired. Again, the manifold alert 146 may be maximized within the working tile 118. The header of the manifold alert 146 may include textual and graphical information, and selectable options 144.

Figure 10:
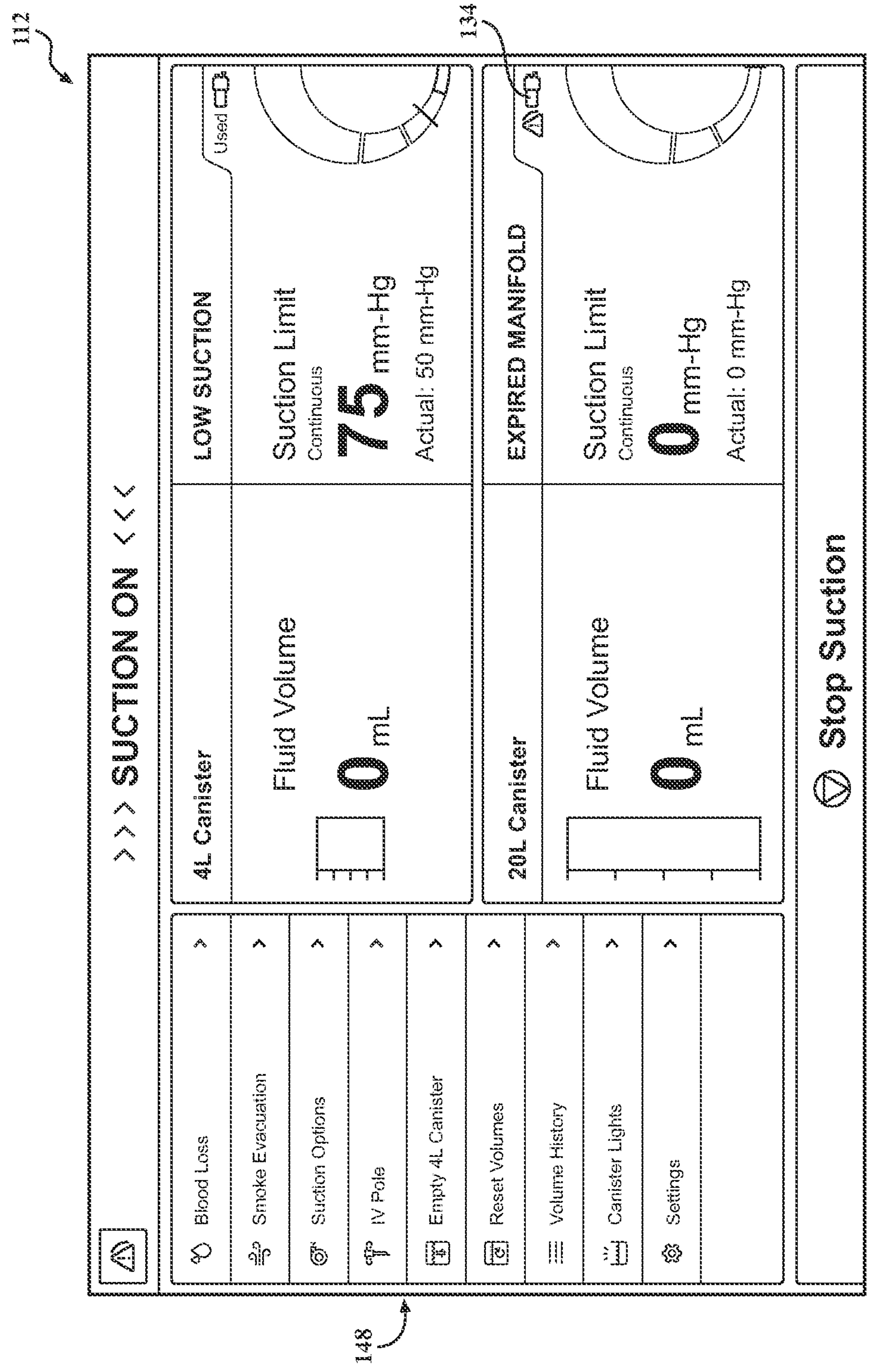
FIG. 10 illustrates a seventh exemplary configuration of the user interface for the medical waste collection system.

Referring now to FIG. 10, the working tile 118 and the toolbar 120 are configured to cooperate to provide intuitive visualization of the statuses and selectable options of the features of the medical waste collection system 100. The arrangement also permits the first canister tile 114 and the second canister tile 116 to remain statically positioned on the user interface 112, as those are reflective of the primary function of the medical waste collection system 100. Selecting any one of the icons of the toolbar 120 may be configured to maximize a toolbar menu 148 within the working tile 118. The toolbar menu 148 includes textual labels corresponding to the icons of the toolbar 120. Each option of the toolbar menu 148 will be discussed in turn.

Returning again to FIGS. 4-6, the user interface 112 is configured to display blood loss data. The blood loss data may be obtained through means internal or external to the medical waste collection system 100. As mentioned, the receivers 110 may removably receive a cartridge and include sensors for sensing an optical characteristic of the waste material, or a recirculation path may be provided within the chassis 102 in which sensors measure a concentration of a blood component within the waste material as disclosed in commonly-owned International Application No. PCT/US2022/047685, filed Oct. 25, 2022, the entire contents of which are hereby incorporated by reference. Additionally or alternatively, the medical waste collection system 100 may receive blood loss data from other systems, including but not limited to sponge management systems sold under the tradename Triton by Gauss Surgical, Inc. (Menlo Park, Calif.) and SurgiCount by Stryker Corporation. The blood loss may also be manually inputted to the user interface 112 or another user interface within the medical facility.

A blood loss icon 154 may be selected from the toolbar 120 or the toolbar menu 148, after which a blood loss tile 156 is maximized within the working tile 118. Further, the blood loss icon 154 remains visually emphasized to indicate which of the options of the toolbar menu 148 is being displayed as the working tile 118. The blood loss tile 156 may display a suction blood volume 150 indicative of the blood loss data obtained through means integrated with the medical waste collection system 100. Further, in combination with the external means or manual input of the blood loss data, the working tile 118 may provide for a cumulative blood volume 152. The cumulative blood volume 152 is updated in real-time during operation of the medical waste collection system 100. For example, FIGS. 5 and 6 show an increasing amount of the cumulative blood volume 152 with increased waste volume in the upper waste canister 106.

Figure 11:
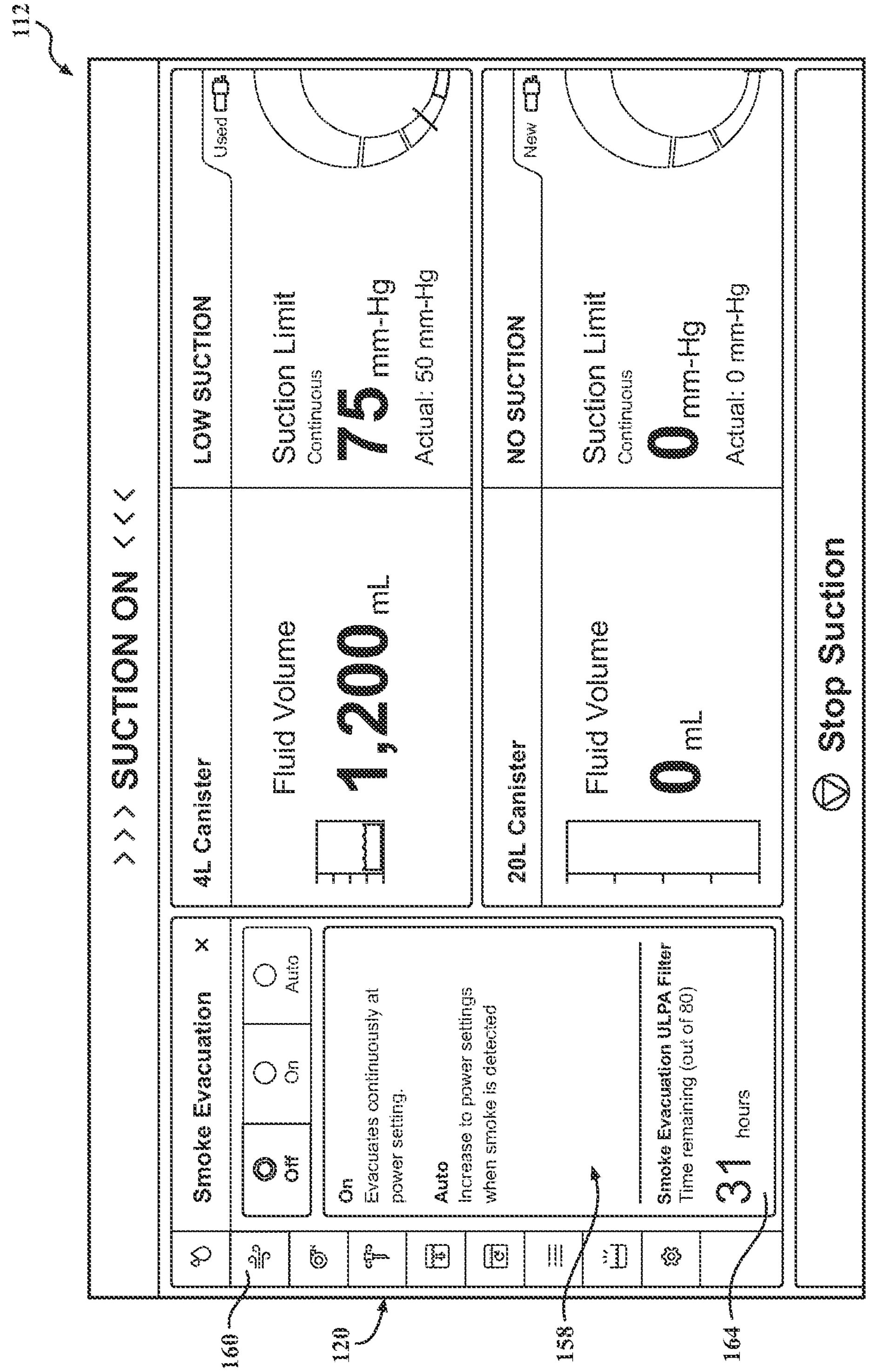
FIG. 11 illustrates an eighth exemplary configuration of the user interface for the medical waste collection system.
Figure 12:
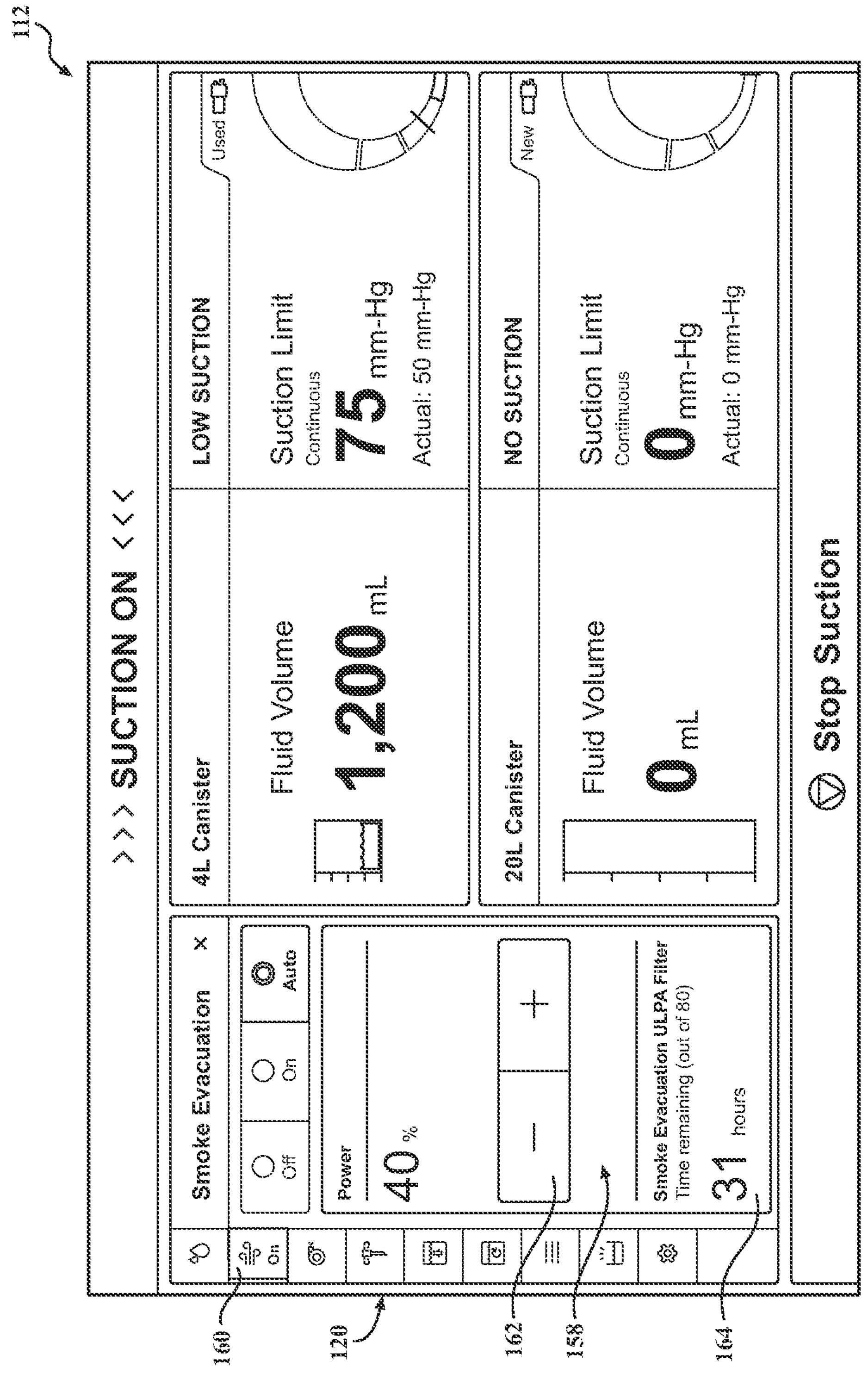
FIG. 12 illustrates a ninth exemplary configuration of the user interface for the medical waste collection system.

Referring now to FIGS. 11 and 12, a smoke evacuation tile 158 is displayed on the user interface 112 with selection of a smoke evacuation icon 160. The smoke evacuation tile 158 may provide selectable options to operate the smoke evacuation subsystem 109 in one of a "on" mode and an "auto" mode. In the "auto" mode, the smoke evacuation tile 158 may include selectable options to select a power setting 162 to which a smoke evacuation pump (not identified) is to be powered at upon detection of smoke with a sensor. The smoke evacuation tile 158 may also display a timer 164 indicative of the running time for which a smoke evacuation filter (not identified) has been used.

Figure 13:
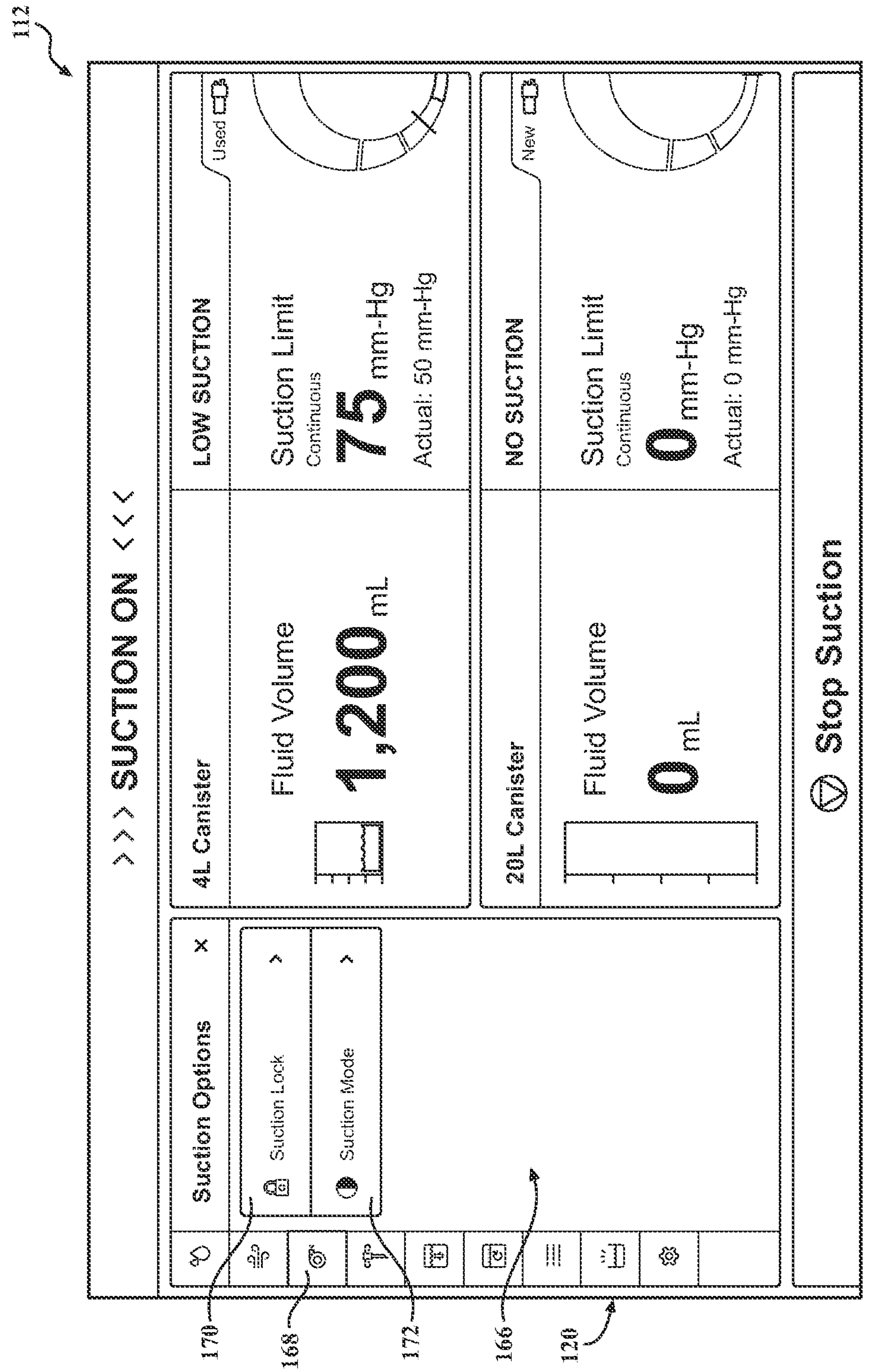
FIG. 13 illustrates a tenth exemplary configuration of the user interface for the medical waste collection system.
Figure 14:
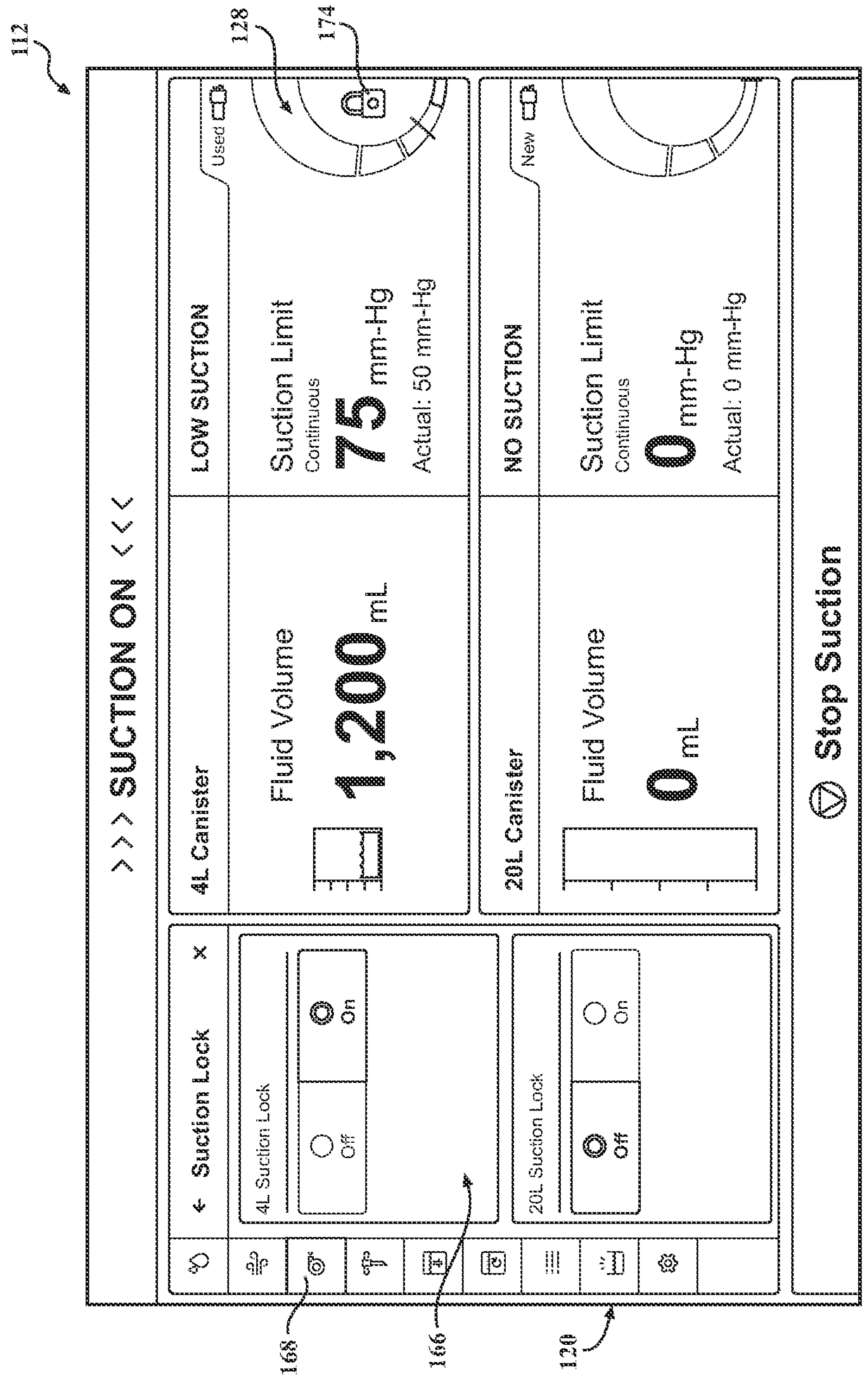
FIG. 14 illustrates an eleventh exemplary configuration of the user interface for the medical waste collection system.
Figure 15:
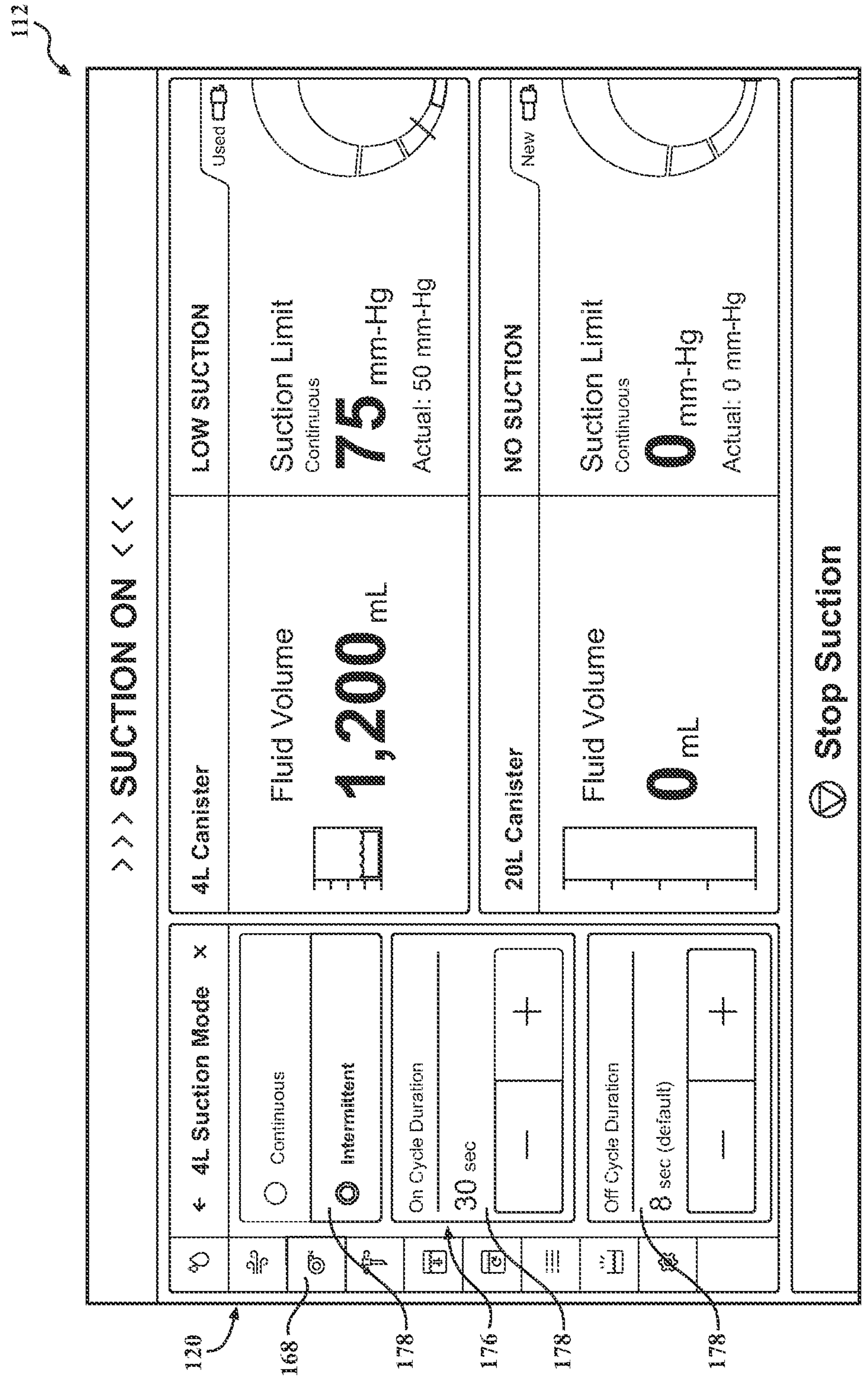
FIG. 15 illustrates a twelfth exemplary configuration of the user interface for the medical waste collection system.

FIGS. 13-15 show a suction options tile 166 being displayed on the user interface 112 with selection of a suction options icon 168. The suction options tile 166 may include selectable options including a suction limit lock 170 and a suction mode 172. With concurrent reference to FIGS. 7 and 8, the suction limit lock 170 is configured to set a maximum vacuum level in which the user may set as the suction limit. In other words, the user may adjust the suction limit as desired up to the suction limit lock. Attempts to increase the suction limit beyond the suction limit lock may not be realized or effectuated by the controller 113. The feature is particularly well suited for applications in which there is a known maximum vacuum level that should almost certainly not be exceeded throughout the procedure. Examples include a pediatric procedures and procedures involving sensitive tissues in which relatively lower suction levels may be utilized. With the suction limit lock activated, a suction limit lock icon 174 is displayed. For example, FIGS. 7, 8, and 14 show the suction limit lock icon 174 as a padlock positioned adjacent to the vacuum meter 128. In the example of FIG. 14, the user may adjust the suction limit up to but not to exceed 75 mmHg. Of course, the user would therefore be unable to adjust the actual vacuum level to exceed 75 mmg. In some instances, the controller 113 may store data associating maximum suction levels associated with a number of predetermined clinical procedures. The user may select a clinical procedure being performed and the controller 113 may automatically set the suction limit lock to the maximum suction level associated with the selected procedure.

Figure 35:
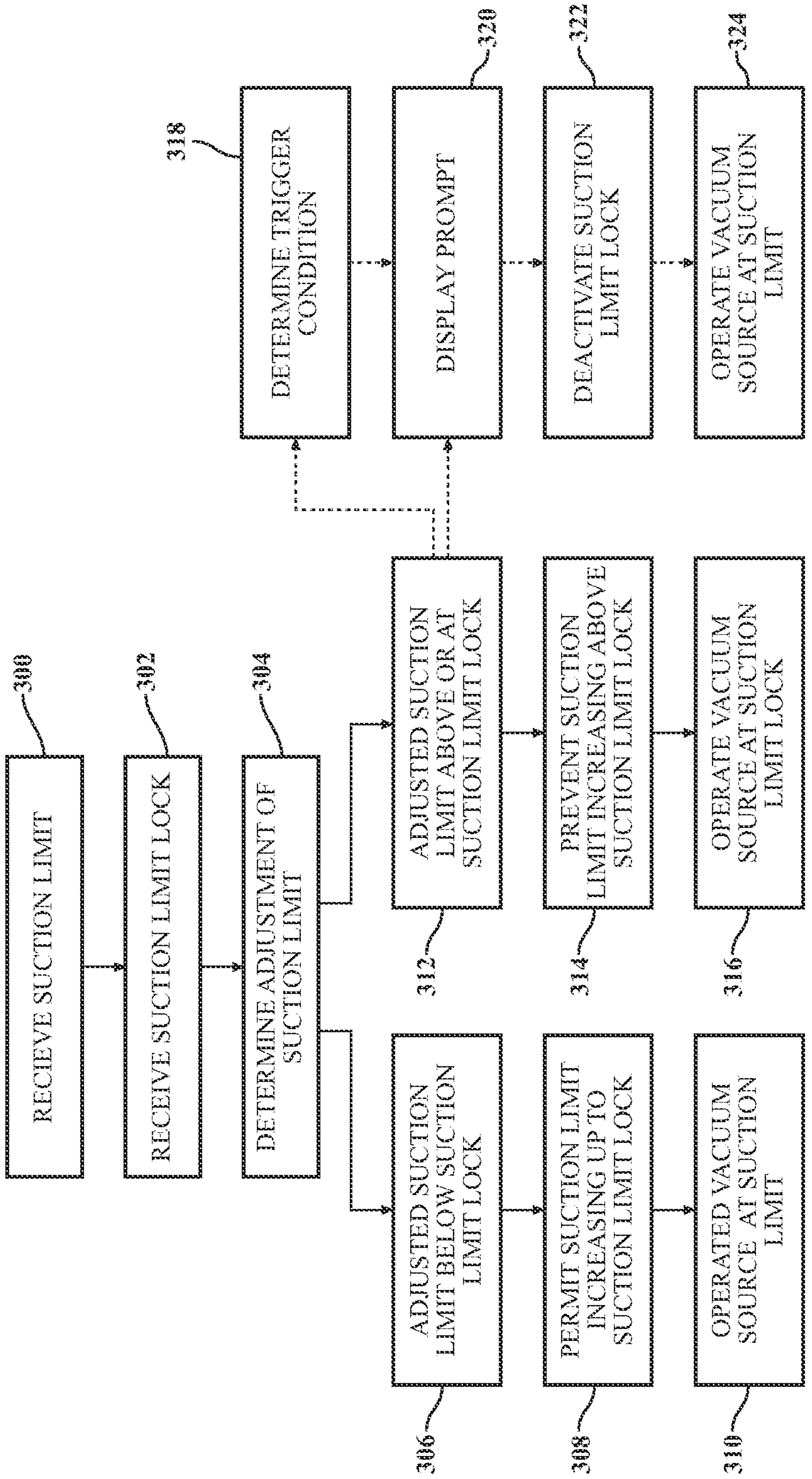
FIG. 35 is a flow chart of a method of performing protocols according to a first aspect of the present disclosure.

Referring to FIG. 35, an exemplary method of operation of the medical waste collection system 100 employing the suction limit lock is illustrated. The method includes the step of receiving a suction limit (step 300) from the user via the user interface 112. The user may adjust the suction limit by rotating the knob 117 adjacent the user interface 112. The controller 113 then operates the vacuum source 119 to establish an actual vacuum level in the associated waste canister 106, 107 equal to the suction limit set by the user. The method may further include the step of receiving a suction limit lock (step 302) from the user. The user may set the suction limit lock as described above at the current suction limit or at a preset level. After the suction limit lock is established, the user may attempt to adjust the suction limit. The method may further include the step of determining whether the adjustment of the suction limit is above the suction limit lock (step 304). If the controller 113 determines the adjusted suction limit is below the suction limit lock (step 306), the controller 113 permits the suction limit to increase up to the suction limit lock (step 308). The controller 113 then operates the vacuum source 119 to adjust the actual vacuum level to the suction limit (step 310). If the controller 113 determines the suction limit is above or at the suction limit lock (step 312), the controller 113 prevents the suction limit from increasing above the suction limit lock (step 314). The controller 113 then operates the vacuum source 119 up to the suction limit lock (step 316).

In some instances, the user may wish to set the suction limit above the suction limit lock and deactivate the suction limit lock. For instance, the user may have finished a portion of a procedure where suction was being applied near sensitive tissue and may wish to operate vacuum source 119 at a higher vacuum level. It can be difficult during the procedure to navigate through menus quickly to turn the suction limit lock off. To assist the user in quickly deactivating the suction limit lock, the controller 113 may determine that the user wishes to do so by determining a trigger condition has occurred (step 318). In some implementations the trigger condition may be a speed at which the user attempts to increase the suction limit (e.g., speed that the user rotates the knob 117) exceeding a predefined threshold speed. In other implementations, the trigger condition may be a number of attempts by the user to increase the suction limit (e.g., discrete rotations of the knob 117) exceeding a predefined threshold number of attempts. The method may further include the step of displaying a prompt (step 320) for the user to deactivate the suction limit lock (step 322). For example, the user may be performing a procedure and intends to deactivate the suction limit lock by knowingly rotating the knob 117 quickly enough for the trigger condition to occur. The user interface 112 may display the suction options tile 166 shown in FIG. 14, regardless of which tile was shown earlier, to prompt the user to deactivate the suction limit lock. The controller 113 then operates the vacuum source 119 to adjust the actual vacuum level to the suction limit (step 324). In other instances where the trigger condition occurs accidentally, the suction options tile 166 may be brought up and the user may continue operating with the suction limit lock on by not deactivating the suction limit lock.

FIG. 15 shows a suction mode tile 176 being displayed on the user interface 112 with selection of the suction mode 172 option from the suction options tile 166. The suction mode tile 176 displays selectable options 178 for the user to operate the medical waste collection system 100 in a continuous suction mode or an intermittent suction mode. The continuous mode, as implied by its name, draws the vacuum at the actual vacuum level in a constant or near-constant manner. The intermittent suction mode includes periods of suction at or near the actual vacuum level separated by periods of no suction. The selectable options 178 of the suction mode tile 176 are configured to receive inputs from the user to select a duration of periods of suction (i.e., "on cycle duration") and a duration of the periods of no suction (i.e., "off cycle duration"). In some instances, the controller 113 may store data associating maximum suction levels associated with a number of predetermined clinical procedures. The user may select a clinical procedure being performed and the controller 113 may automatically limit the suction limit to the maximum suction level associated with the selected procedure and the controller 113 may operate the vacuum source 119 to include periods of suction at the maximum suction level separated by periods of no suction.

Figure 36:
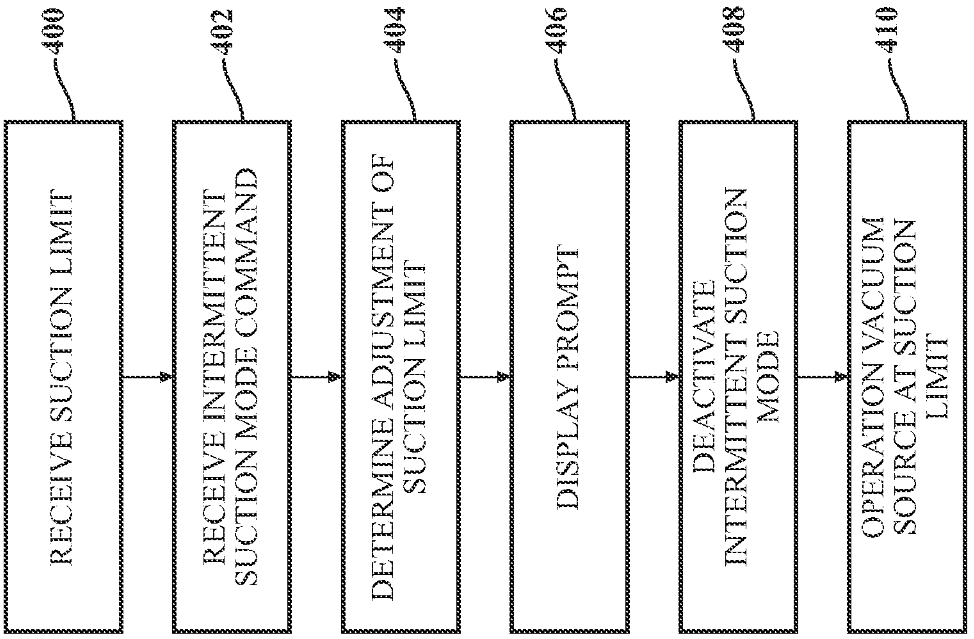
FIG. 36 is a flow chart of a method of performing protocols according to a second aspect of the present disclosure.

Referring to FIG. 36, an exemplary method of operation of the medical waste collection system 100 employing intermittent suction mode is shown. The method includes the step of receiving a suction limit (step 400) from the user via the user interface 112. The user may adjust the suction limit by rotating the knob 117 adjacent the user interface 112. The controller 113 then operates the vacuum source 119 to establish an actual vacuum level in the associated waste canister 106, 107 equal to the suction limit set by the user. The method may further include the step of receiving an intermittent suction mode command (step 402) from the user to operate the vacuum source 119 in intermittent suction mode. After the vacuum source 119 is operated in intermittent suction mode, the user may attempt to adjust the suction limit. The method may further include the step of determining whether the adjustment of the suction limit has been attempted to be adjusted by the user (step 404).

In some instances, the user may wish to exit intermittent suction mode during a procedure. It can be difficult during the procedure to navigate through menus quickly to turn the intermittent suction mode off. To assist the user in quickly deactivating the intermittent suction mode, the controller 113 may determine that the user wishes to do so by determining a trigger condition has occurred. In some implementations the trigger condition may be the user attempting to adjust the suction limit. In other words, the user may be trained to appreciate that one manner by which the intermittent suction mode can be deactivated is by merely turning the knob 117. Alternatively, the trigger condition may be a speed at which the user attempts to increase or decrease the suction limit exceeding a predefined threshold speed, or a number of attempts by the user to increase or decrease the suction limit exceeding a predefined threshold number of attempts. The method may further include the step of displaying a prompt (step 406) for the user to deactivate the intermittent suction mode (step 408). For example, the user may be performing a procedure and intends to deactivate the intermittent suction mode by knowingly rotating the knob 117 a certain number of times exceeding the predetermined threshold number of attempts for the trigger condition to occur. The user interface 112 may display selectable options 178 shown in FIG. 15, regardless of which tile was shown earlier, to prompt the user to deactivate the intermittent suction mode by operating in a continuous suction mode. The controller 113 then operates the vacuum source 119 to adjust the actual vacuum level to the suction limit (step 410).

Figure 16:
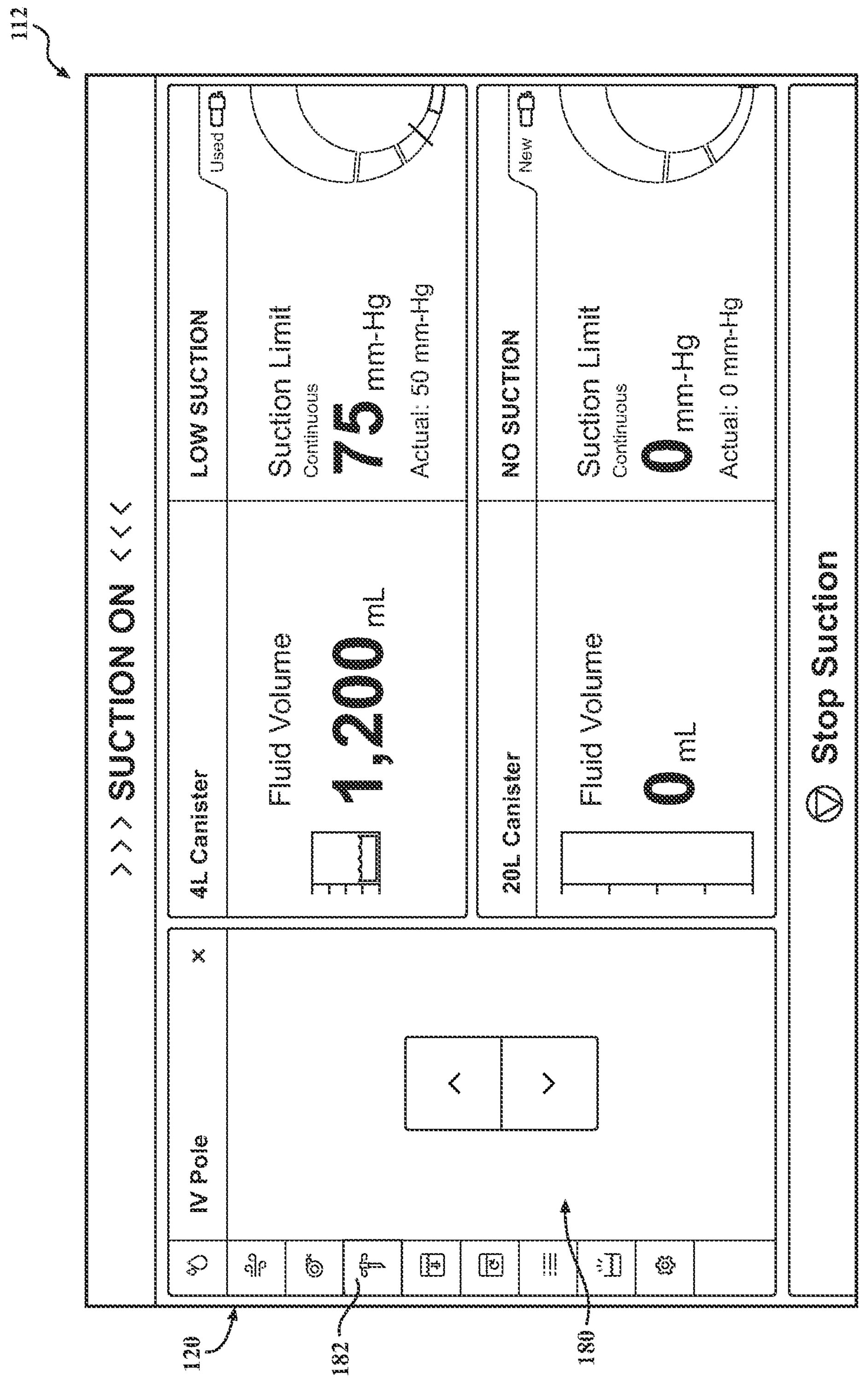
FIG. 16 illustrates a thirteenth exemplary configuration of the user interface for the medical waste collection system.

FIG. 16 shows an IV pole tile 180 being displayed on the user interface 112 with selection of an IV pole icon 182. Further input to the IV pole tile 180 is configured to permit the user to selectively adjust a height of the IV pole assembly 108 supported on the chassis 102.

Figure 17:
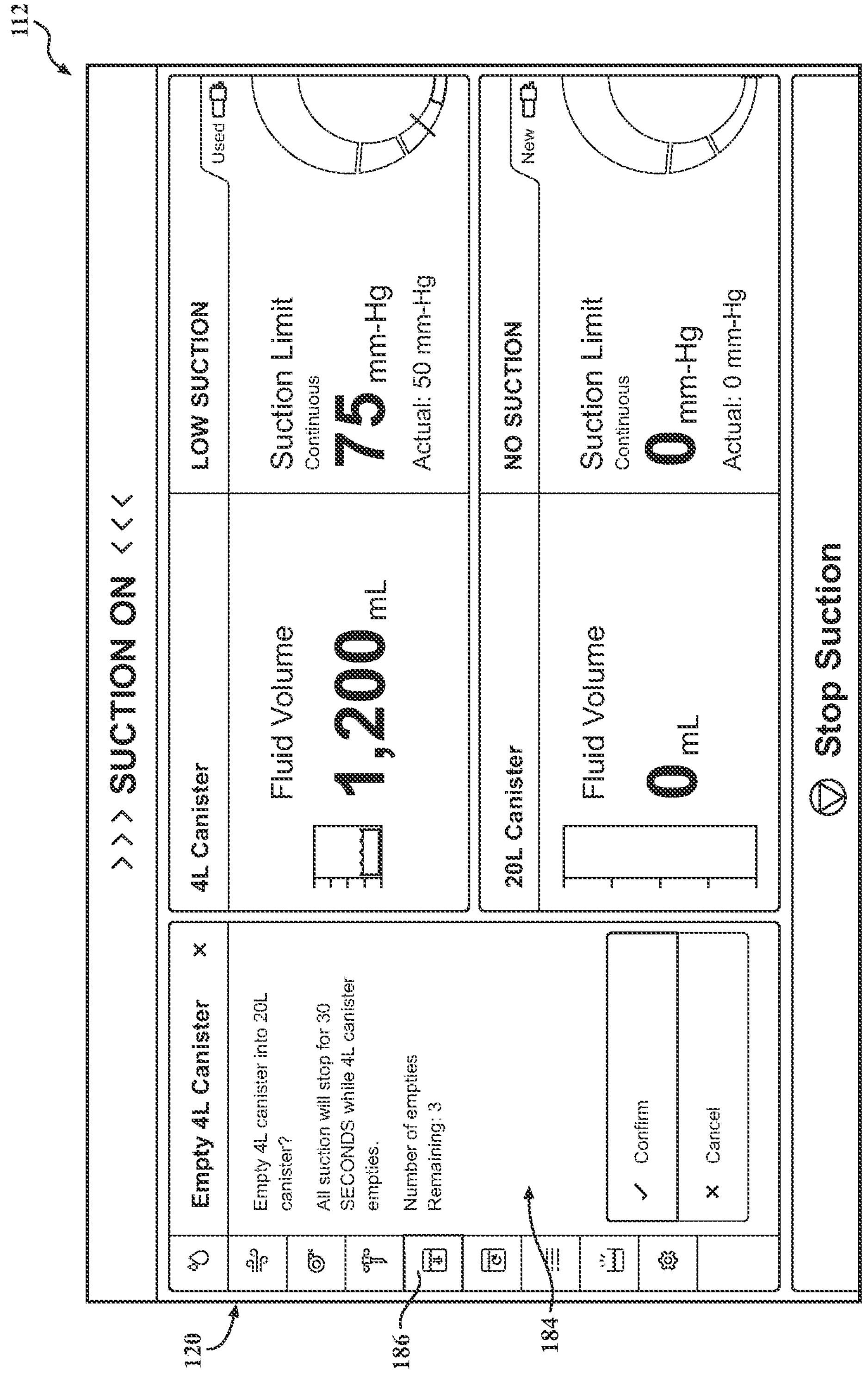
FIG. 17 illustrates a fourteenth exemplary configuration of the user interface for the medical waste collection system.

FIG. 17 shows an empty canister tile 184 being displayed on the user interface 112 withy selection of an empty canister icon 186. Further input to the empty canister tile 184 is configured to actuate the transfer valve to permit the waste material within the upper waste canister 106 to be emptied into the lower waste canister 107. This may be in response to receiving the canister volume alert 142 (see FIG. 7), or as otherwise desired.

Figure 18:
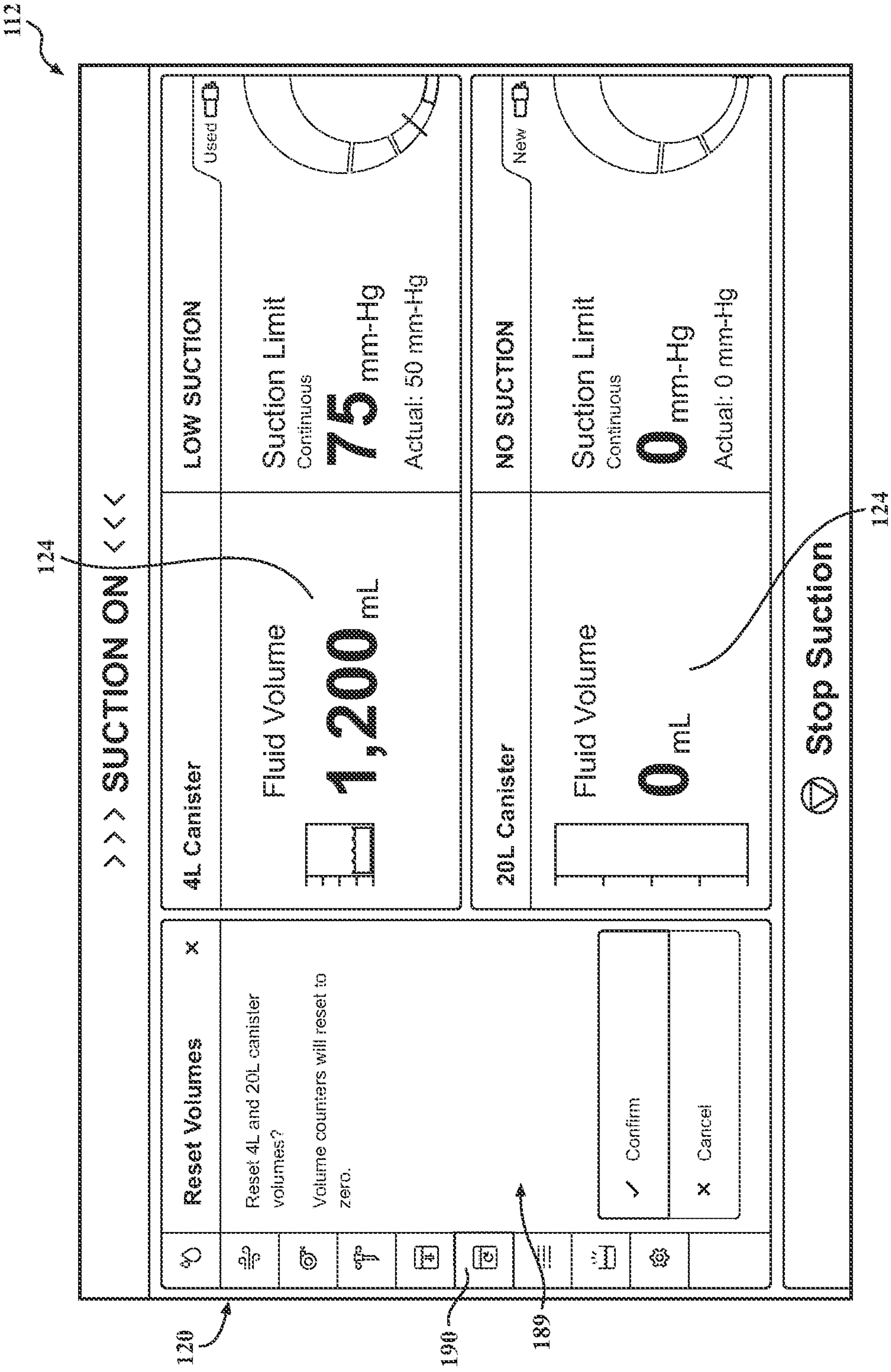
FIG. 18 illustrates a fifteenth exemplary configuration of the user interface for the medical waste collection system.

FIG. 18 shows a reset volume tile 188 being displayed on the user interface 112 with selection of a reset volume icon 189. Further input to the reset volume tile 188 is configured to reset waste volumes displayed on the volume field 124 on the user interface 112 to zero. This may be in response to a non-zero volume being displayed after docking, or as otherwise desired.

Figure 19:
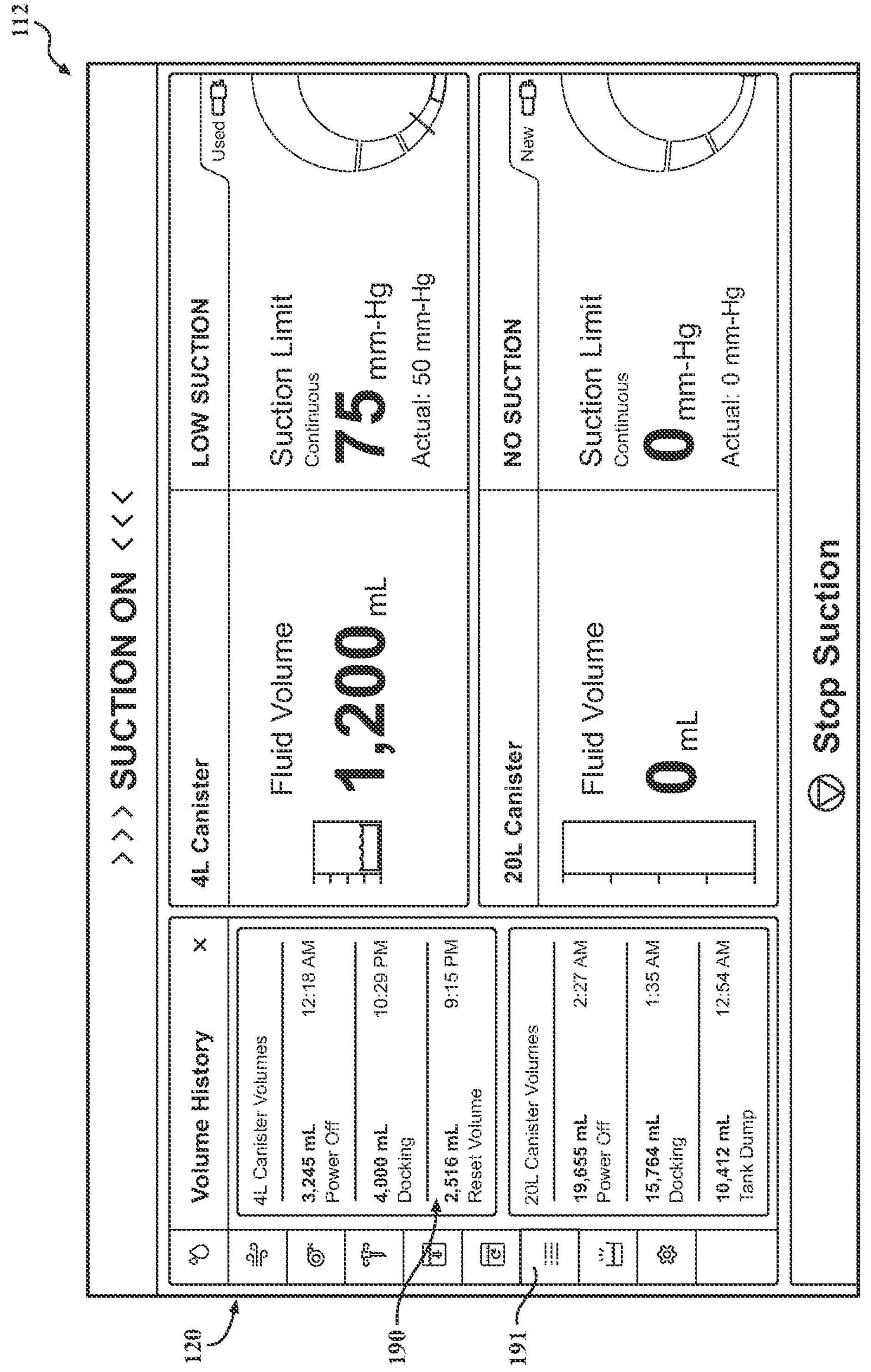
FIG. 19 illustrates a sixteenth exemplary configuration of the user interface for the medical waste collection system.

The occurrences of the upper waste canister 106 being emptied into the lower waste canister 107, the volumes being reset, and other events (e.g., powering off the medical waste collection system 100, performing a docking, etc.) are logged into memory. Those events can be viewed in an event history tile 190 displayed on the user interface with upon selection of an event history icon 191. FIG. 19 shows the event history tile 190 including a description of the event, a date stamp, and a change in volume for each of the events for each of the upper and lower waste canisters 106, 107. The event history tile 190 may also be useful should the user inadvertently reset the canister volumes, for example, before recording the total volume of fluid suctioned for the surgical procedure.

Figure 20:
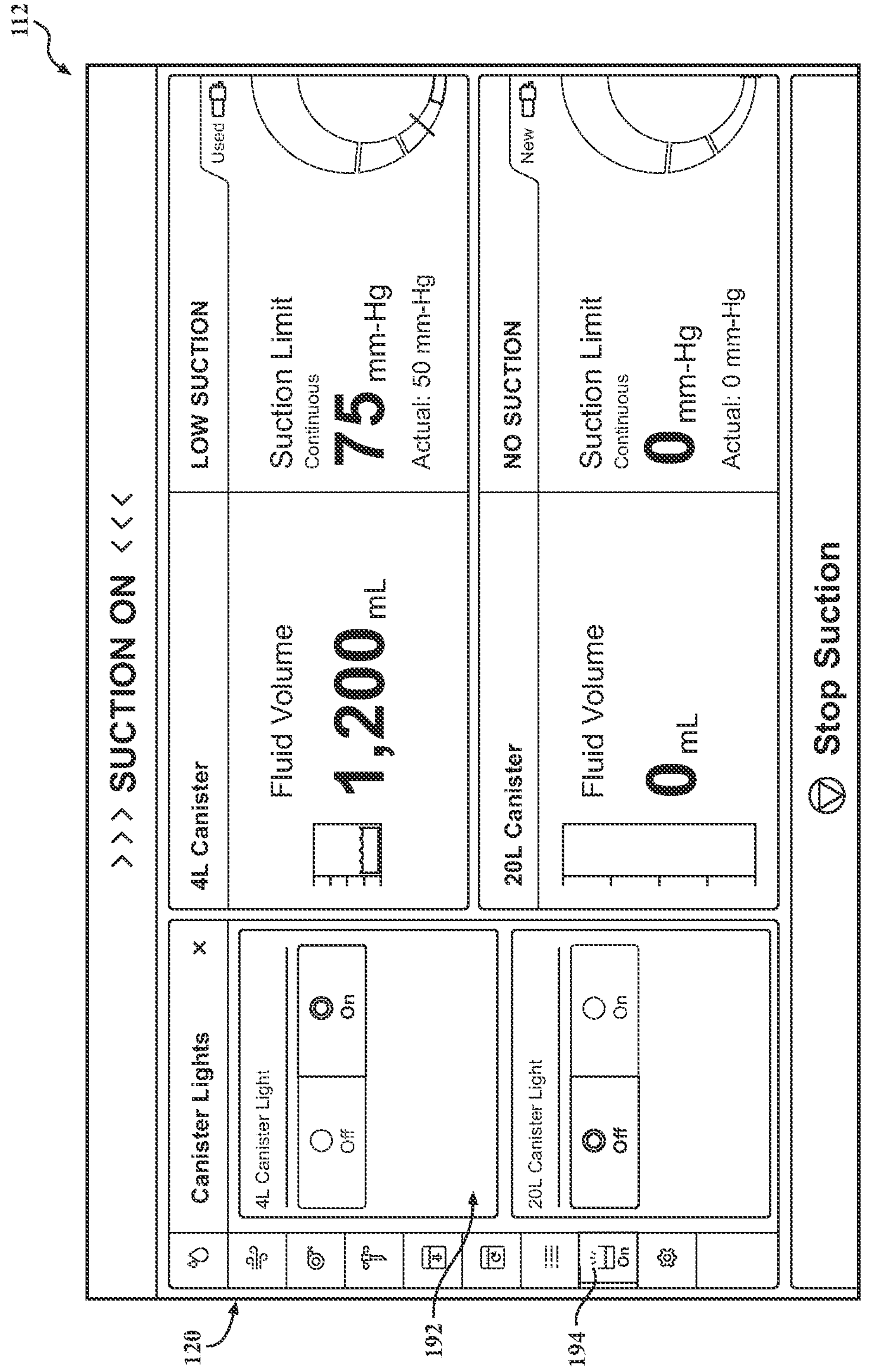
FIG. 20 illustrates a seventeenth exemplary configuration of the user interface for the medical waste collection system.
Figure 21:
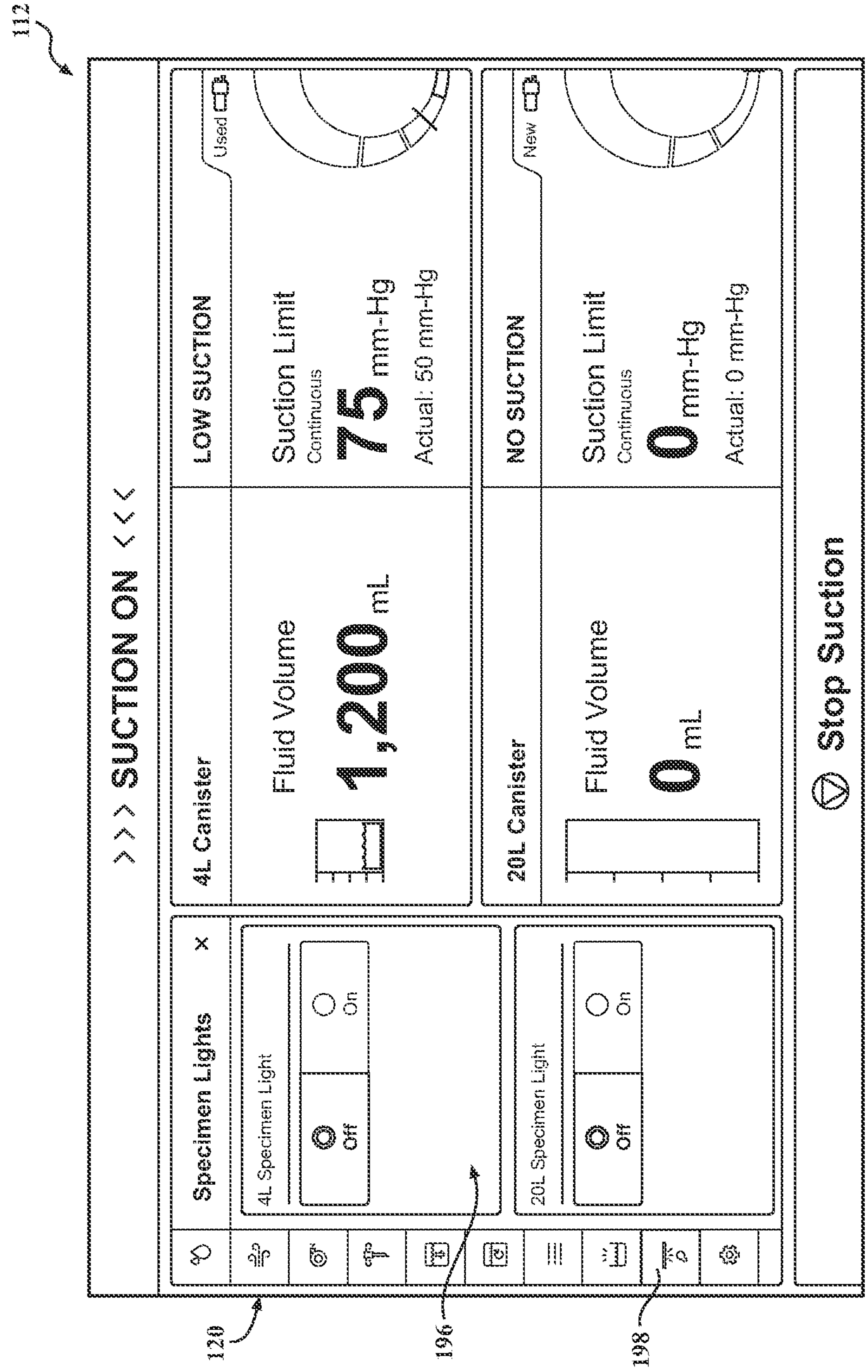
FIG. 21 illustrates an eighteenth exemplary configuration of the user interface for the medical waste collection system.

FIG. 20 shows a canister light tile 192 being displayed on the user interface 112 upon selection of a canister light icon 194. Further input to the canister light tile 192 is configured to actuate the canister lights disposed within a respective one of the upper waste canister 106 and the lower waste canister 107. In certain implementations, the medical waste collection system 100 includes specimen lights (not identified), such as those disclosed in commonly-owned International Publication No. 2020/210763, published Oct. 15, 2020, the entire contents of which are hereby incorporated by reference. FIG. 21 shows a specimen light tile 196 being displayed on the user interface 112 with selection of a specimen light tile 198. Further input to the specimen light tile 196 is configured to actuate the specimen lights. It is further contemplated that the medical waste collection system 100 may include manifold lights, and a manifold light tile may be displayed.

Figure 22:
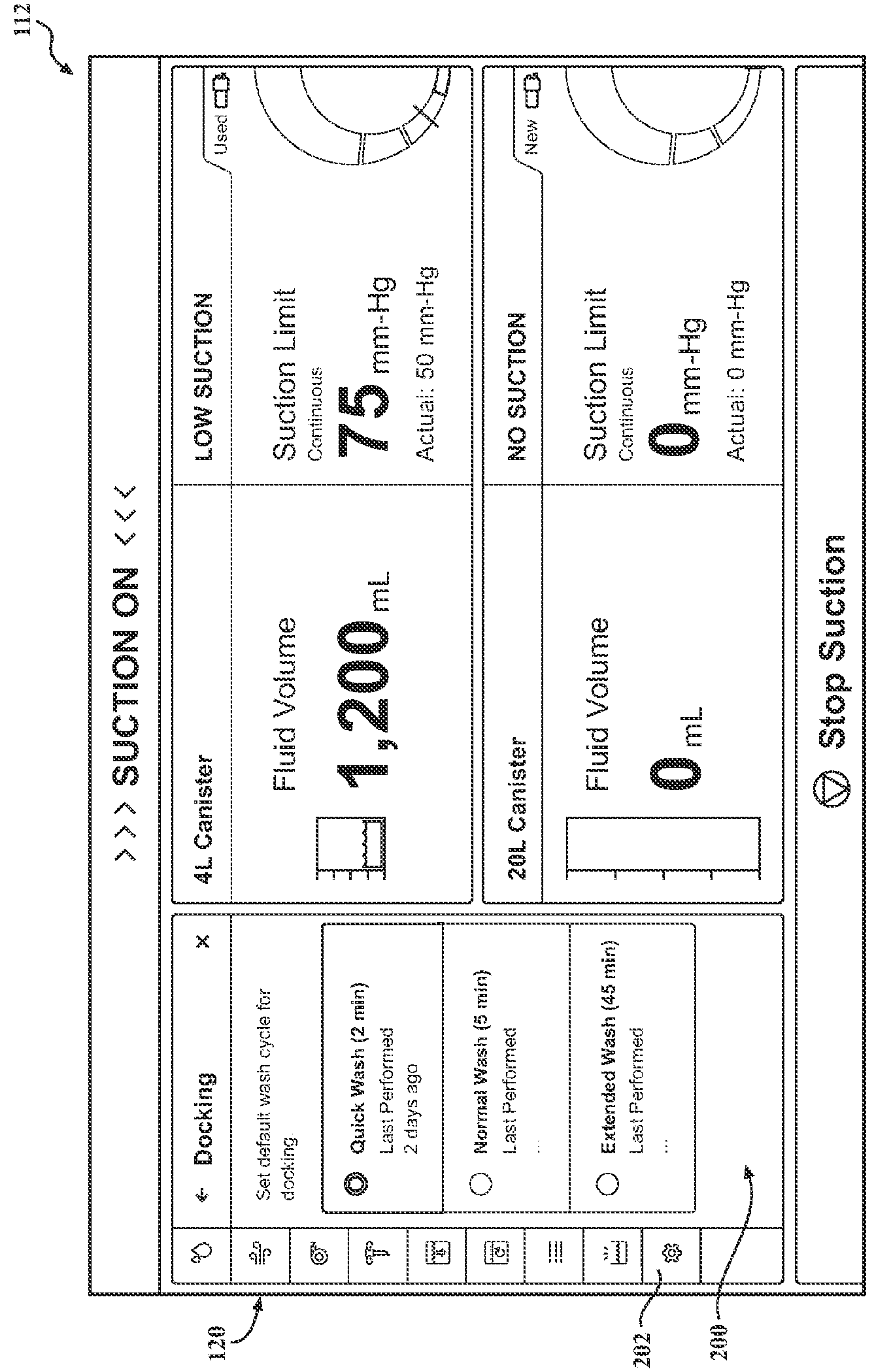
FIG. 22 illustrates a nineteenth exemplary configuration of the user interface for the medical waste collection system.
Figure 23:
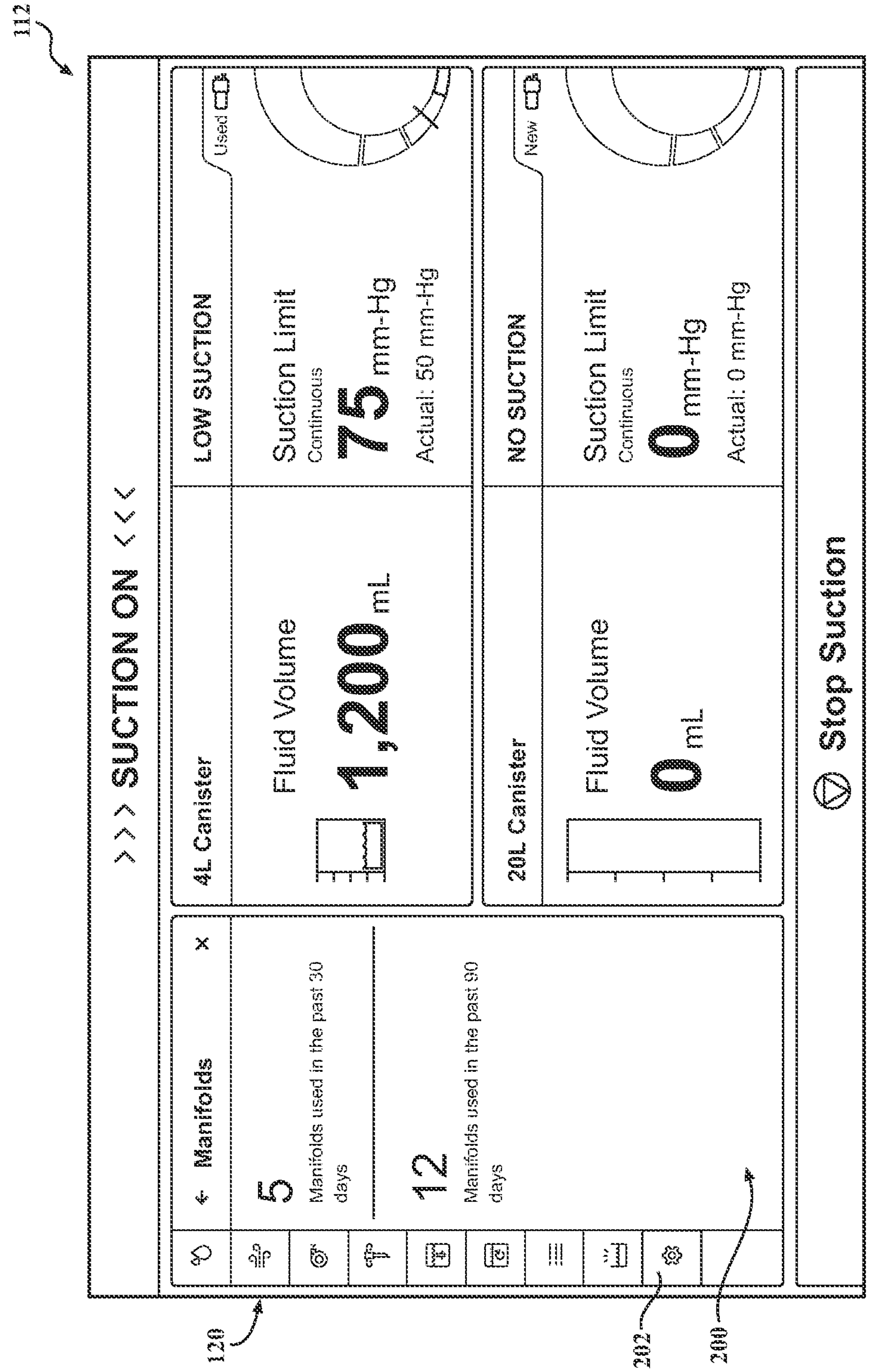
FIG. 23 illustrates a twentieth exemplary configuration of the user interface for the medical waste collection system.
Figure 24:
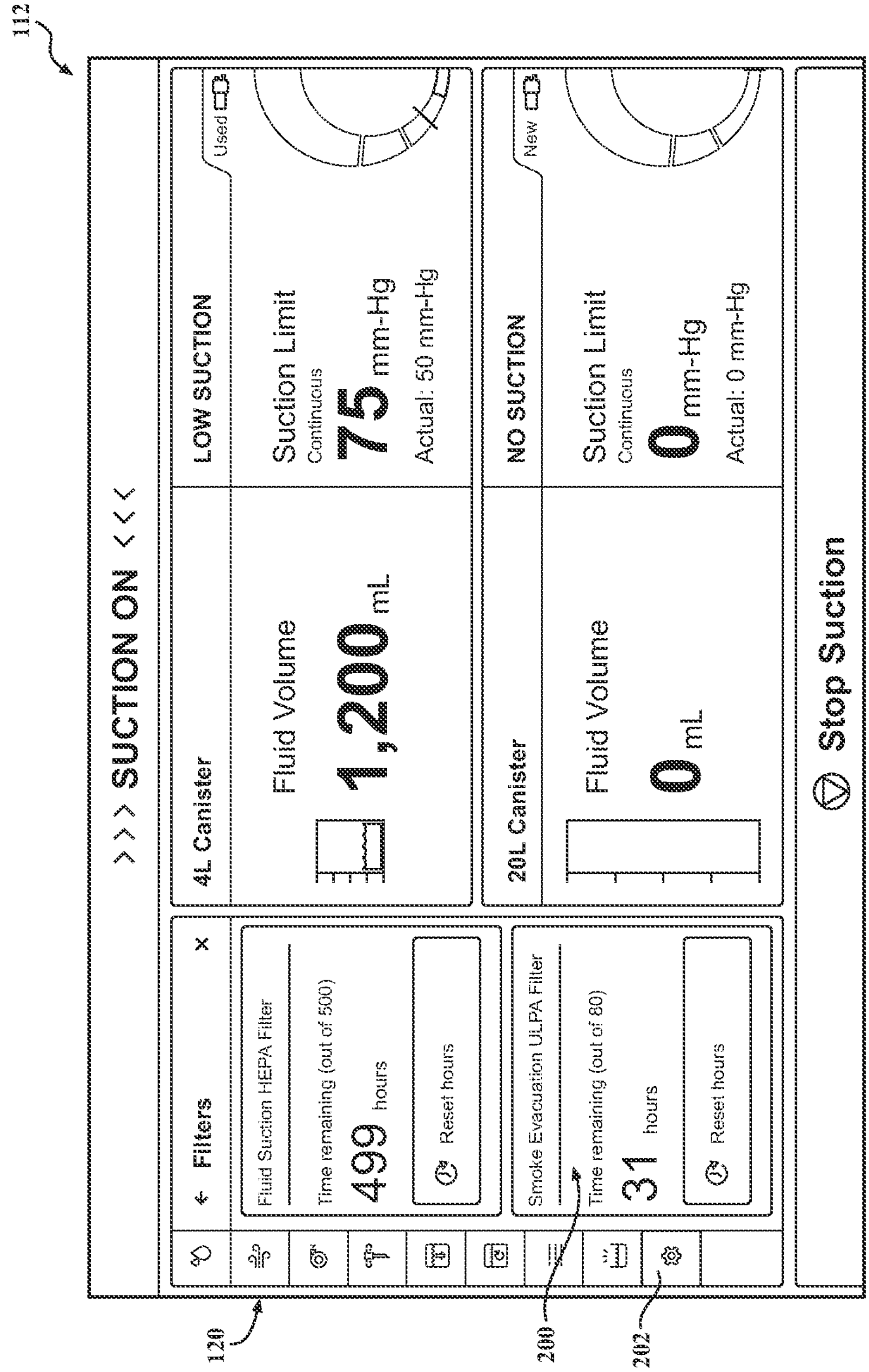
FIG. 24 illustrates a twenty-first exemplary configuration of the user interface for the medical waste collection system.
Figure 25:
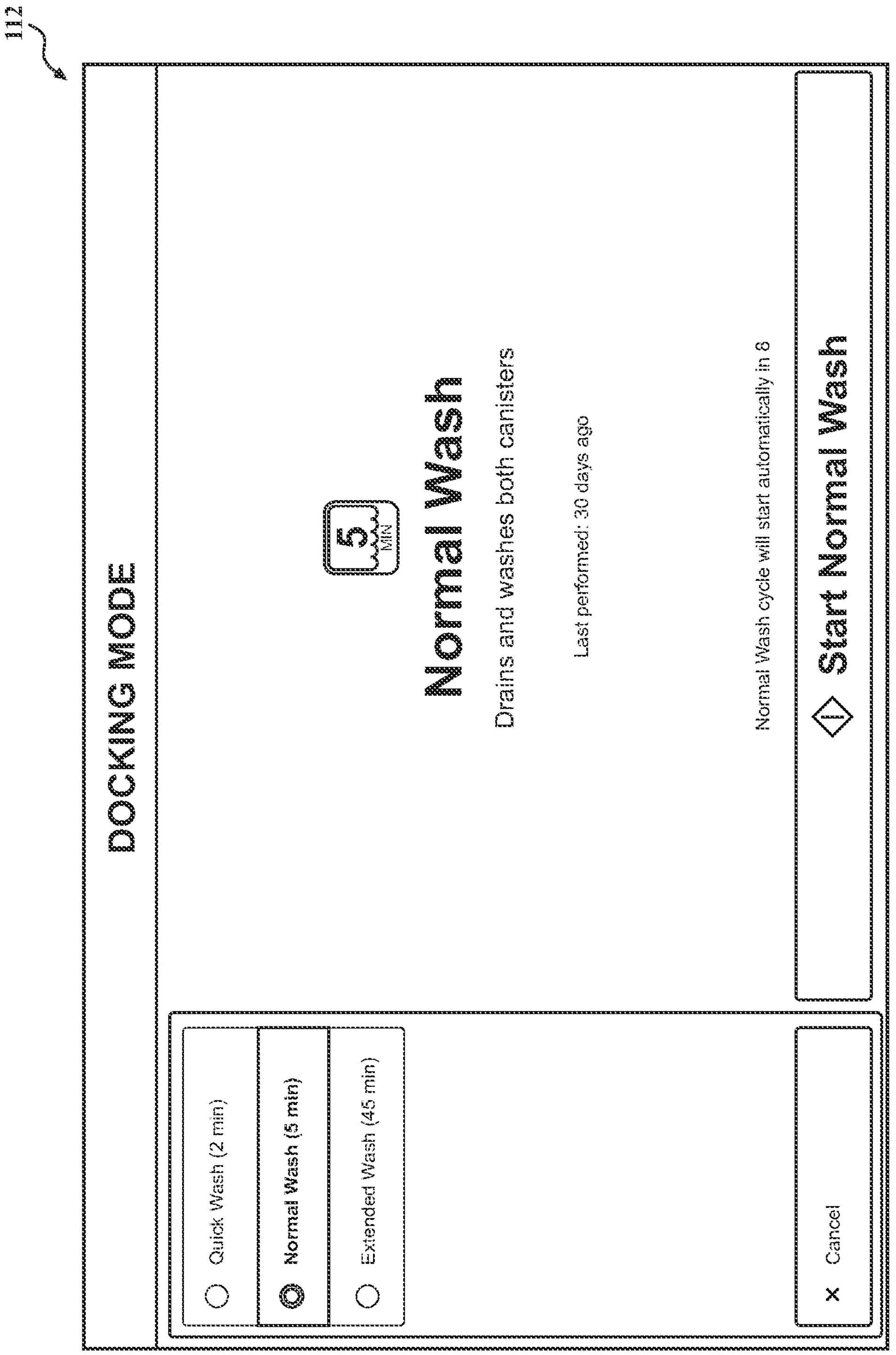
FIG. 25 illustrates a twenty-second exemplary configuration of the user interface for the medical waste collection system.

FIGS. 22-24 show settings tiles 200 being maximized within the working tile 118 with selection of a setting icon 202, and FIG. 25 shows the user interface 112 in a docking mode in which one of the cleaning modes may be selected, started, and stopped. The settings tile 200 of FIG. 22 includes selectable options to receive an input for the user to set a default leaning mode. Upon coupling the chassis 102 with the docker, the medical waste collection system 100 and docker may operate in the default cleaning mode. Further, an indication of the last instance the medical waste collection system 100 was docked and cleaned in each of the cleaning modes may be provided. The settings tile 200 of FIG. 23 includes information indicative of a frequency of manifold usage over a particular duration, for example, thirty or ninety days. The settings tile 200 of FIG. 24 includes information indicative of filter status for one or both of a main filter supported on the chassis 102 and the smoke evacuation filter of the smoke evacuation subsystem. Selectable options may be presented to receive user inputs to reset the filter status information, for example, upon changing the filter(s).

Referring back to FIGS. 1 and 2, the housing 105 comprises a front portion 204, a back portion 206 opposite the front portion 204, and side portions therebetween. Each of the front and back portions 204, 206 of the housing 105 may comprise a single panel or multiple panels. The front portion 204 of the housing 105 has an exterior surface. The exterior surface of the front portion 204 may be adapted to generally face the patient during the medical procedure. The front portion 204 of the housing 105 may have a window 208 to permit a user to view the waste canisters 106, 107. When the waste canisters 106, 107 comprise a transparent material such as glass, the user may be able to see the waste material in at least one of the waste canisters 106, 107 through the window 208 or alternatively, a level of the waste material in at least one of the waste canisters 106, 107. When the waste canisters 106, 107 comprise a transparent or translucent material, the user can see a level of waste material in the waste canister 40. In the configuration illustrated in FIGS. 27A and 27B, the window 208 is shown generally in the center (side to side) of the front portion 204 of the housing 105. However, it is contemplated that the window 208 may be disposed off-center such that the window 208 is disposed to the left or right of the position of the window 208 as viewed in FIGS. 27A and 27B.

Figure 27A:
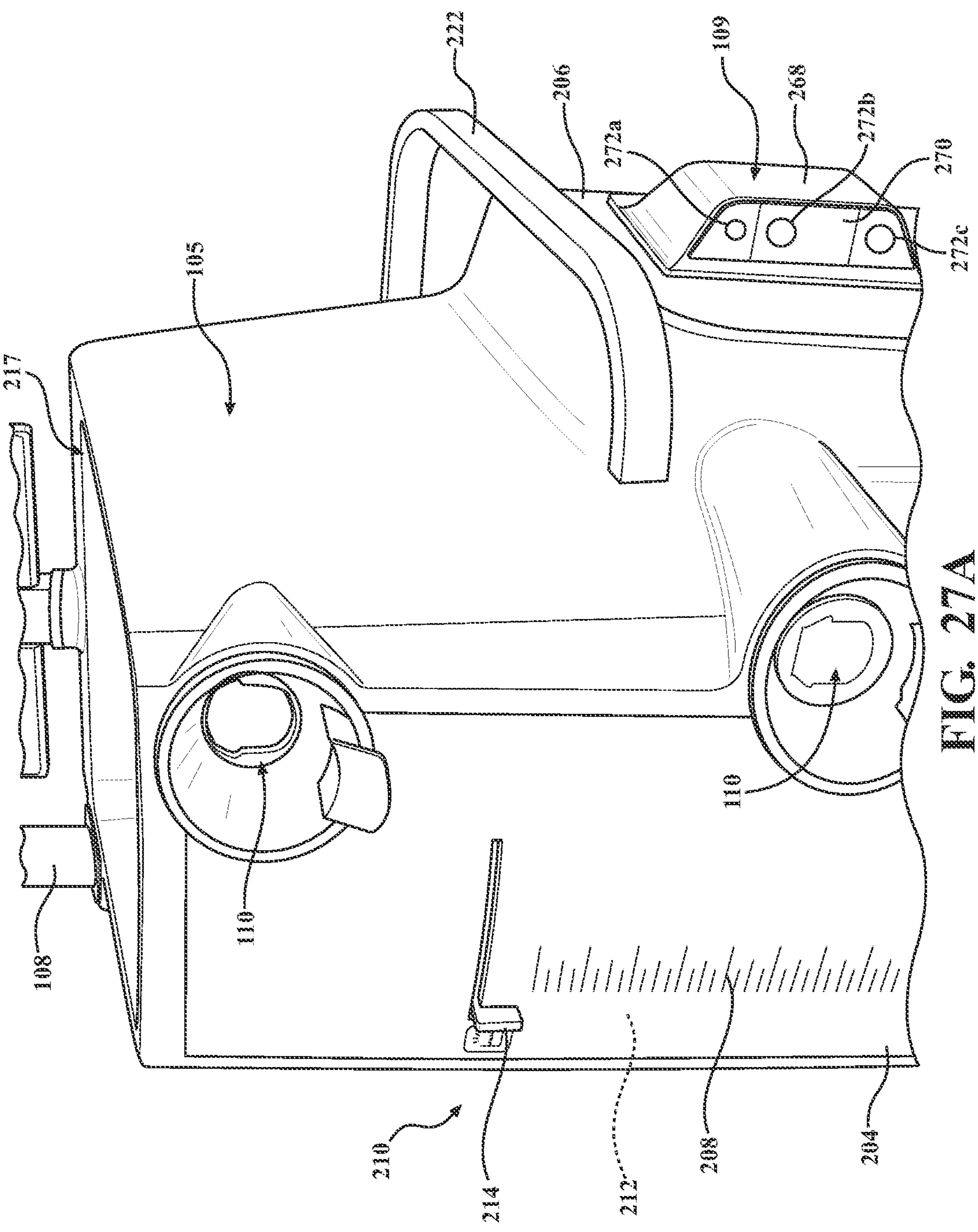
FIG. 27A is a partial perspective view of the medical waste collection system with a cover of a cover assembly in a first state.
Figure 27B:
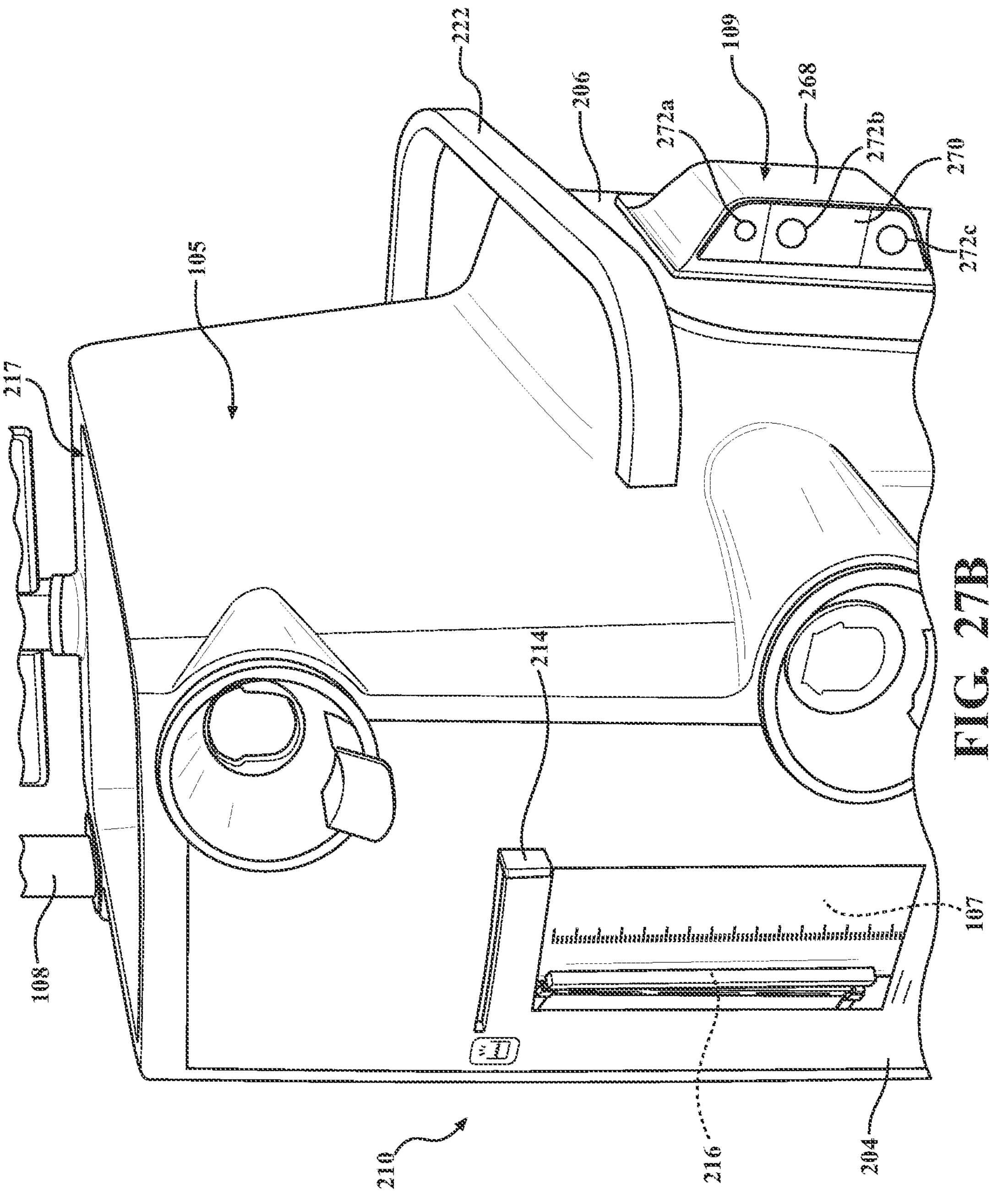
FIG. 27B is a partial perspective view of the medical waste collection system with the cover of the cover assembly in a second state.

Referring to FIGS. 27A and 27B, the medical waste collection system 100 may comprise a cover assembly 210 for selectively permitting a user to view the waste canisters 106, 107, through the window 208. The cover assembly 210 may be coupled to the housing 105. The cover assembly 210 may include a cover 212 moveable between a first position where the cover 212 occludes the window 208 and a second position where the cover 212 at least partially does not occlude the window 208. The cover assembly 210 may further include an actuator (e.g., a switch, lever, etc.) 214 selectively moveable between a first position (FIG. 27A) and a second position (FIG. 27B). In the first position of the actuator 214, the cover 212 is in the first position. In the second position of the actuator 214, the cover 212 is in the second position. The cover 212 may comprise a single body that is moveable relative the housing 105 to reveal one or more waste canisters 106, 107 with a single continuous movement of one actuator 214. One or both of the waste canisters 106, 107 may be positioned within the housing 105 to permit the cover to at least partially move around, and sometimes behind, the waste canisters 106, 107, while moving the cover to the second position. In some configurations, a single cover 212 may be used to permit and prevent viewing of both the waste canisters 106, 107. In other configurations, the separate covers 212 may be employed for each of the waste canisters 106, 107.

Referring to FIG. 27B, the medical waste collection system 100 may be configured to be illuminated internally to assist the user in observing the level of waste material in the waste canisters 106, 107. In one configuration, the medical waste collection system 100 includes a light source assembly 216 coupled to the chassis 102 and configured to project light onto at least one of the waste canisters 106, 107. In some configurations, the light source assembly 216 may be coupled to one of the waste canisters 106, 107 to project light into the associated waste canister 106, 107. In one configuration, the light projected is a low-intensity light. The light source assembly 216 may comprise a plurality of light sources to illuminate the waste canisters 106, 107. However, it is also contemplated that the light source assembly 216 could instead comprise a single light source for illuminating the waste canisters 106, 107. The light source assembly 216 may comprise one or more light sources selected from a light emitting diode, a bulb, a lamp, or another like device configured to emit visible light. In the configuration illustrated, the light source assembly 216 is configured to project light away from the front portion 204 of the housing 105. It is contemplated that the light source assembly 216 may be positioned elsewhere relative to the waste canisters 106, 107 such that the light source assembly 216 projects light onto or into the waste canisters 106, 107 in a different direction. Providing the light source assembly 216 mitigates the need for an external lighting source such as a flashlight.

The light source assembly 216 may be configured to generate light (via the light sources) responsive to the cover 212 being in the second position. Said differently, the light source assembly 216 may be configured to automatically illuminate the waste canisters 106, 107 should the user open the cover 212 to expose the waste canisters 106, 107. A sensor (e.g., a hall effect sensor) may be coupled to one of the housing 105 and the cover 212. The sensor may be configured to generate a signal responsive to movement of the cover 212 from the first position to the second position. The controller 113 may be coupled to the sensor and the light source assembly 216. The controller 113 may receive the signal from the sensor to operate the light source assembly 216 to illuminate one or both the waste canisters 106, 107 responsive to the cover 212 moving from the first position to the second position. In some configurations, the controller may operate the light source assembly 216 to provide variable light intensity to illuminate the waste canisters 106, 107 based on a degree to which the cover 212 has moved from the first position. For instance, the controller 113 may be configured to operate the light source assembly 216 to illuminate the waste canisters 106, 107 at a brighter intensity when the cover 212 reveals the entire window 208 than when the cover 212 is partially occluding the window 208.

Figure 28:
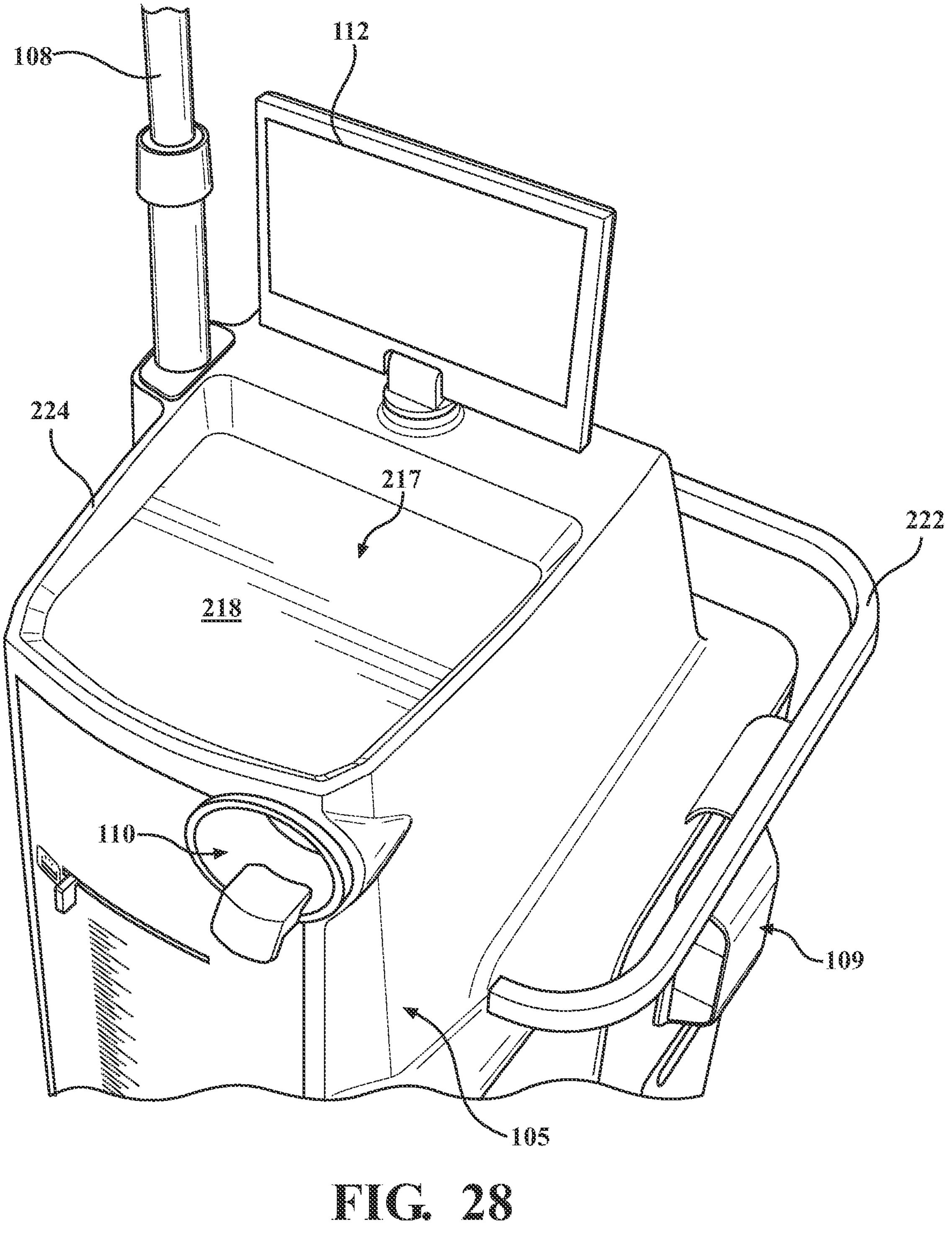
FIG. 28 is a top perspective view of the medical waste collection system.
Figure 29:
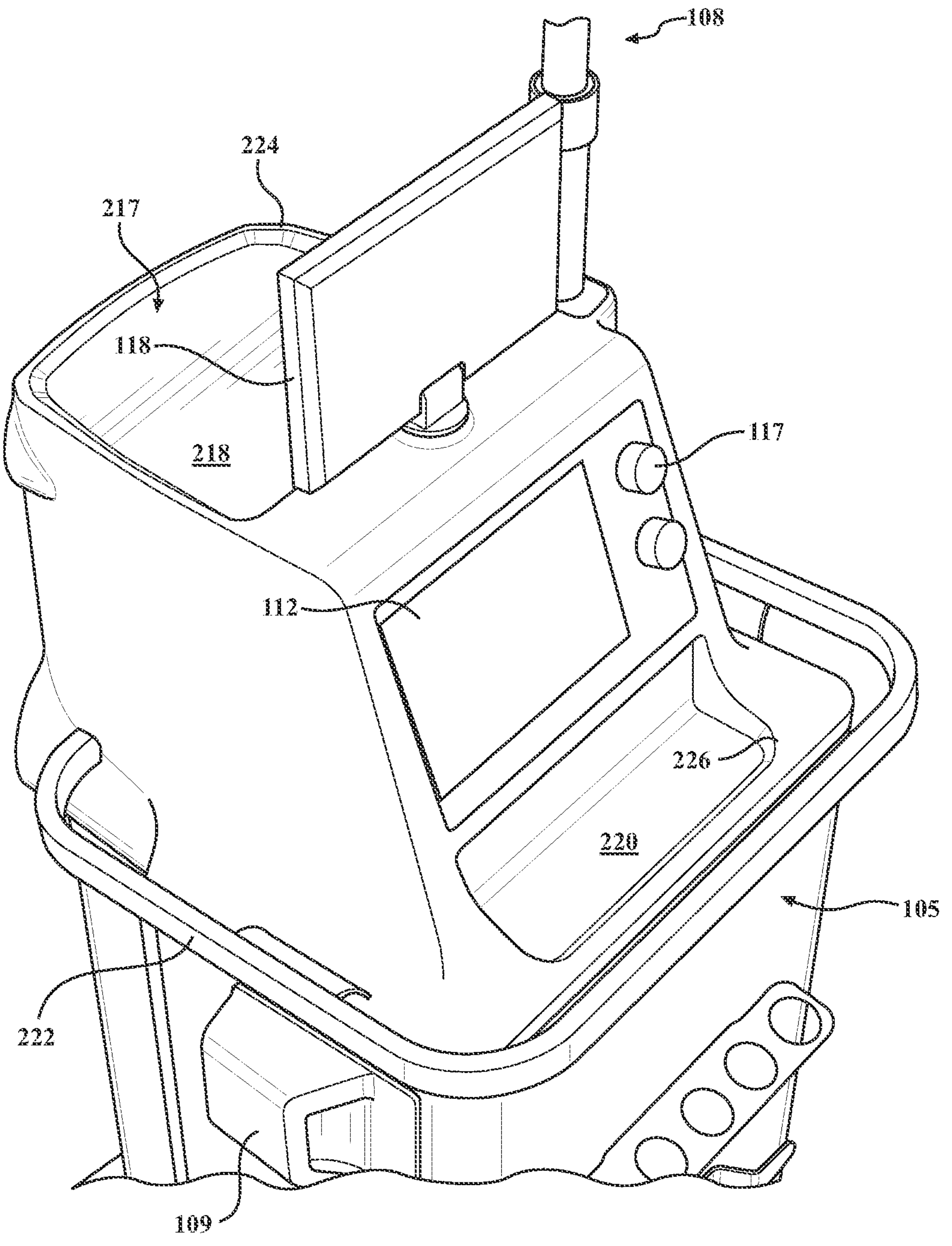
FIG. 29 is another top perspective view of the medical waste collection system.

Referring to FIGS. 28 and 29, the housing 105 includes a top portion 217 disposed between the front and back portions 204, 206 of the housing 105. The top portion 217 of the housing 105 may include work surfaces 218, 220 for supporting a variety of medical tools and equipment. One of the work surfaces 218, 220 is disposed above and below a caregiver interface 222, described in further detail below. In other configurations, the work surfaces 218, 220 may both be disposed above or below the caregiver interface 222. The work surfaces 218, 220 may be generally planar and parallel to the floor surface. Said differently, the work surfaces 218, 220 may be generally planar and configured to be level with respect to gravity when resting. Further, the work surfaces 218, 220 may be set into the top portion 217 of the housing 105. The top portion 217 of the housing 105 may have sidewalls 224, 226 at least partially surrounding the work surfaces 218, 220, respectively. In some configurations, the sidewalls 224, 226 and the work surfaces 218, 220 are integral or monolithic, respectively, such that fluid spilled or otherwise disposed on the work surfaces 218, 220 cannot leak into the interior of the housing 105. In some implementations, the sidewalls 224, 226 surrounding the work surfaces 218, 220 may be sloped to deter users from setting equipment on the housing 105 that does not fit on the work surfaces 218, 220.

Figure 30:
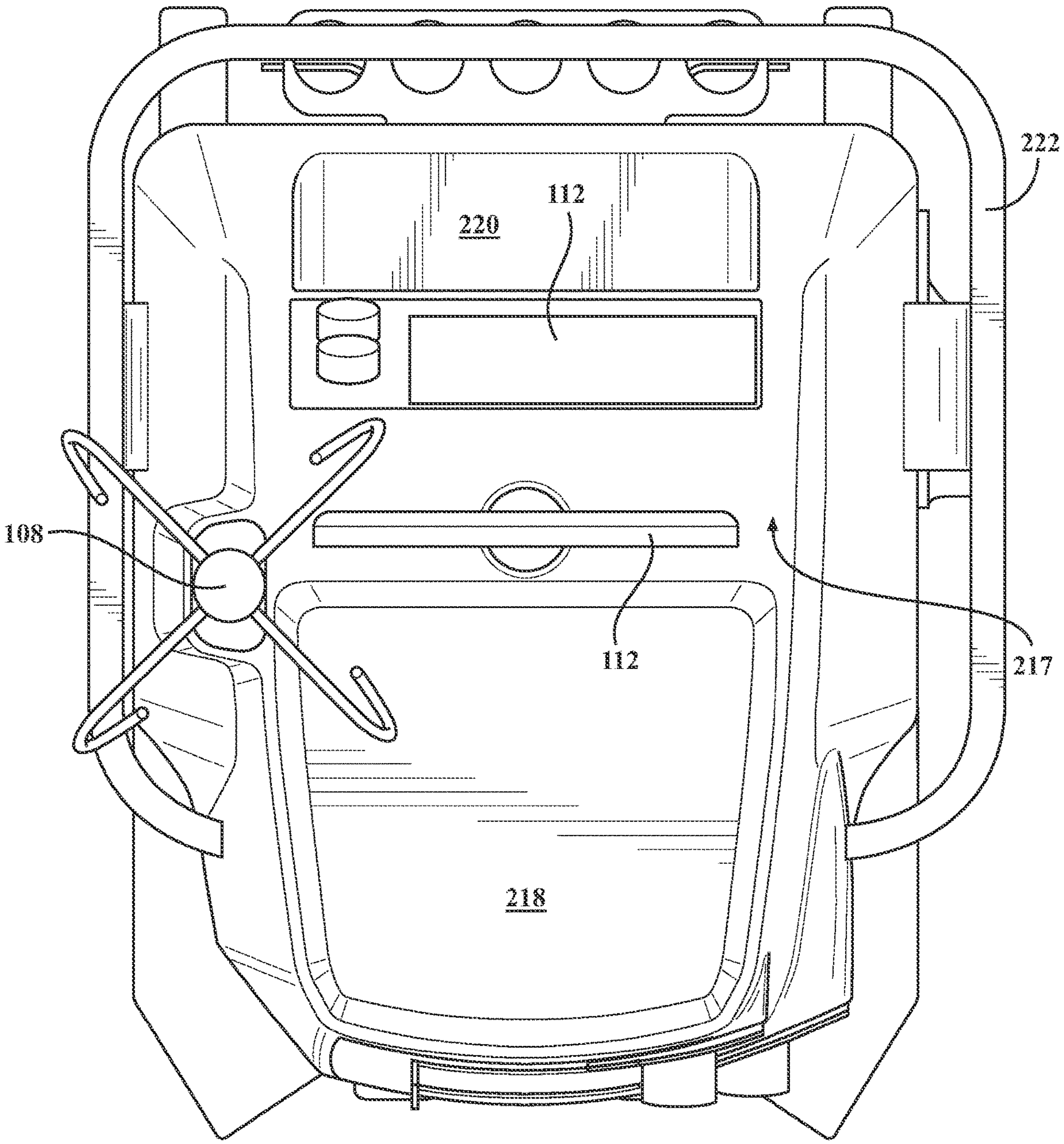
FIG. 30 is a plan view of the medical waste collection system.

Referring to FIG. 30, the medical waste collection system 100 may include a caregiver interface 222, such as a handle, that at least partially surrounds the housing 105 of the medical waste collection system 100. The caregiver interface 222 may extend about at least three sides of the housing 105 to be easily graspable regardless of the position of the caregiver relative to the medical waste collection system 100. The caregiver interface 222 may be spaced from the housing 105 to facilitate movement of the medical waste collection system 100 between use areas, and between the use areas and a docking station. In some configurations the caregiver interface 222 may have a width of between 20 inches and 23 inches. The width may be defined as a width of two portions of the caregiver interface 222 that extend on opposite sides of the housing 105 and/or chassis. Thus, the user may move the medical waste collection system 100 around the health care facility to collect waste material generated during medical procedures performed in different locations throughout the health care facility. The caregiver interface may also be suitable for making small adjustments to the position of the medical waste collection system 100 across the floor surface, such as pulling the medical waste collection system 100 away from a wall of the procedure room when the back portion 206 of the housing 105 is adjacent a wall, or for moving the medical waste collection system 100 when the medical waste collection system 100 needs to be moved laterally. As the caregiver interface extends away from the housing 105, the caregiver interface 222 may also serve as a point of first contact when making incidental contact with external structures, mitigating contact between the housing 105 and the other portions of the medical waste collection system 100 with the external structures.

Figure 31B:
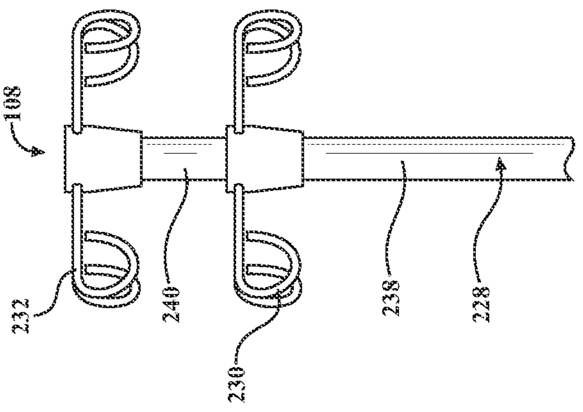
FIG. 31B is a detailed front elevation view of a portion of the medical waste collection system with the first implementation of a support pole assembly.
Figure 31A:
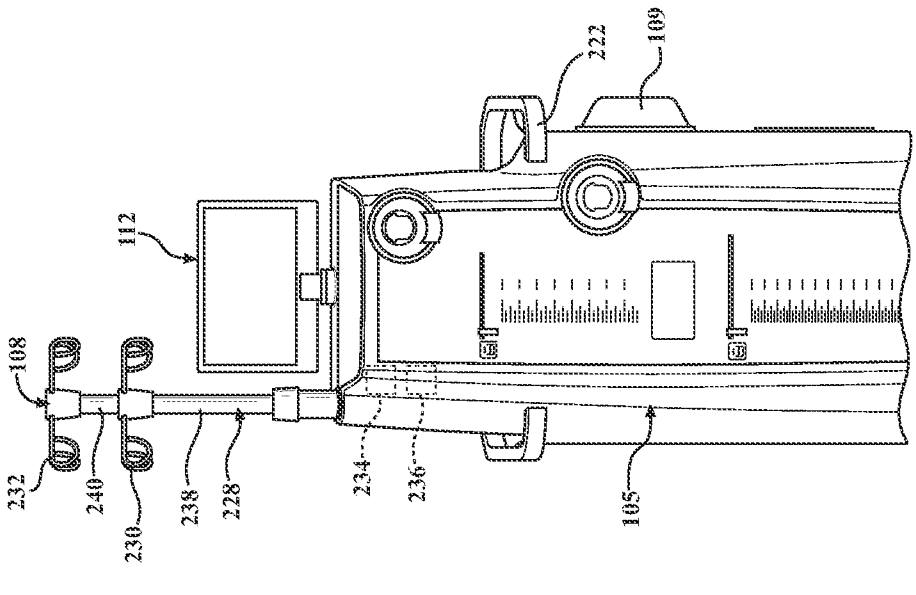
FIG. 31A is a partial front elevation view of the medical waste collection system with a first implementation of a support pole assembly.
Figure 32B:
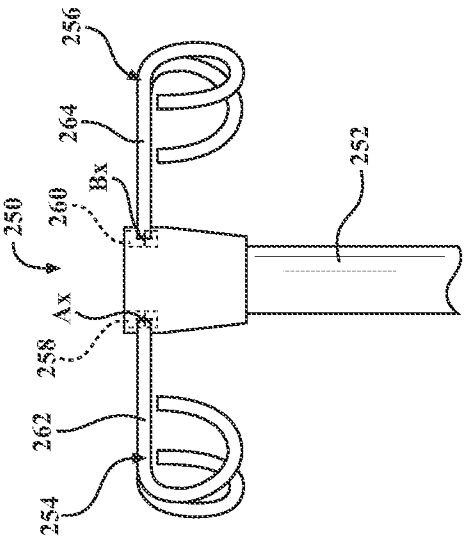
FIG. 32B is a detailed front elevation view of a portion of the medical waste collection system with the second implementation of the support pole assembly in a first position.
Figure 32C:
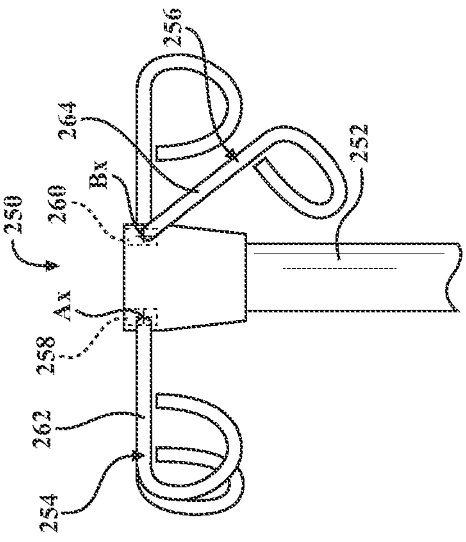
FIG. 32C is a detailed front elevation view of a portion of the medical waste collection system with the second implementation of the support pole assembly in a second position.

Referring to the FIGS. 31A-32C and as briefly referenced above, the medical waste collection system 100 may include a support pole assembly 108 coupled to one or both of the chassis 102 and the housing 105. FIGS. 31A and 31B illustrate a first implementation of the support pole assembly 108 and FIGS. 32A-32C illustrate a second implementation of the support pole assembly 250. The support pole assemblies 108, 250 may be used to support supplemental equipment such as an infusion or intravenous (IV) fluid bag during a medical procedure. The support pole assemblies 108, 250 may comprise an elongated body 228, 252 extending from the chassis 102 along a support pole axis SX. In many configurations the support pole axis SX is oriented vertically with respect to gravity. The support pole assemblies 108, 250 may comprise a first holder 230, 254 disposed at a first elevation with respect to gravity. The support pole assemblies 108, 250 may further include a second holder 232, 256 moveable relative to the first holder 230, 254 to at least a second elevation with respect to gravity different from the first elevation. In some configurations and in some positions of the second holders 232, 256, the first and second holders 232, 256 may be disposed at the same elevation with respect to gravity. One or mor actuators 234, 236, 258, 260 may be coupled to the support pole assemblies 108, 250 for moving at least one of the first and second holders 230, 232, 254, 256 to change the elevation of at least one of the holders 230, 232, 254, 256. The holders 230, 232, 254, 256 may comprise one or more of a hook, a clamp, or a projection for supporting the supplemental equipment. In one configuration where IV bags are used, a caregiver may adjust the relative flow rate between two different IV bags supported by either holder 230, 232, 254, 256 by adjusting the height, i.e., elevation with respect to gravity, of either of the first and second holders 230, 232, 254, 256 relative to the height of the other of the first and second holders 230, 232, 254, 256.

In the first implementation illustrated in FIGS. 31A and 31B, the elongated body 228 comprises telescoping first and second portions 238, 240. Said differently, one of the first and second portions 238, 240 of the elongated body 228 may be slidable within or around the other of the first and second portions 238, 240 to permit one or both of the first and second portions 238, 240 to move axially along the support pole axis SX. One or both the first and second portions 238, 240 may recede inside the chassis 102 or the housing 105 when adjusting the elevation of the first and second holders 230, 232. The first holder 230 is coupled to the first portion 238 and the second holder 232 is coupled to the second portion 240. A first actuator 234 may be coupled to the first portion 238 and the chassis 102 to adjust a height of the first portion 238, and thus the first holder 230, and a second actuator 236 may be coupled to the second portion 240 and the chassis 102 to adjust a height of the second portion 240, and thus the second holder 232. The first and second actuators 234, 236 may be supported by the chassis 102 or housing 105. In some implementations, the first and second actuators 234, 236 may comprise linear actuators to move the first and second portions 238, 240. In other configurations, the actuators 234, 236 may comprise a motor and a gear assembly, pulley, linkage, or belt, etc. to translate torque from the motor into linear movement of the first and second portions 238, 240. In some configurations where a single actuator is employed, only one of the first and second portions 238, 240 may be moveable relative to the other of the first and second portions 238, 240.

Figure 32A:
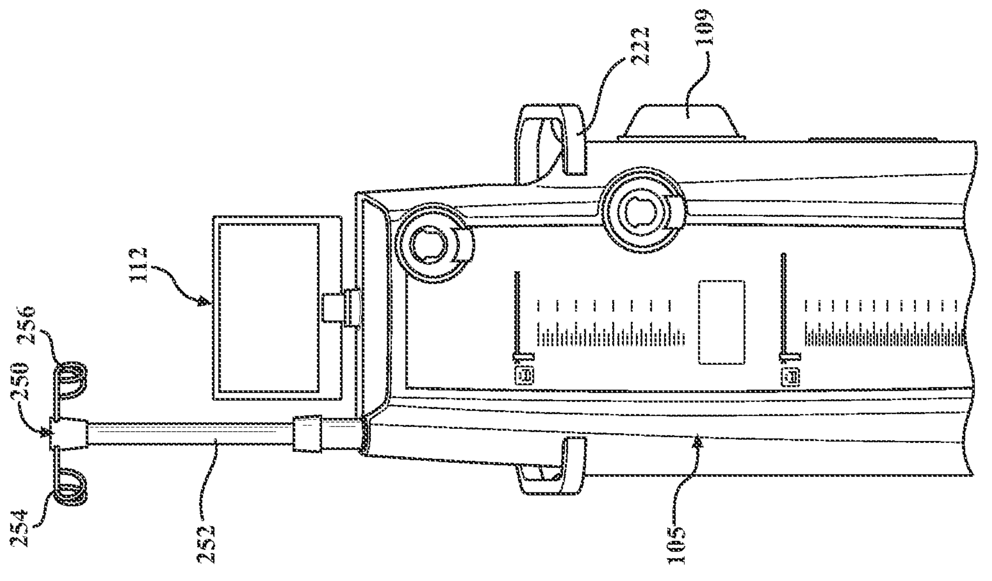
FIG. 32A is a partial front elevation view of the medical waste collection system with a second implementation of the support pole assembly.

In the second implementation illustrated in FIGS. 32A-32C, the support pole assembly 250 comprises at least one pivotable member 262, 264 configured to be pivotably coupled to the elongated body 252 at a proximal end and the associated first and second holders 254, 256, respectively, at a distal end. In the illustrated configuration, the first holder 254 is coupled to a first pivotable member 262 and configured to pivot about a first axis AX and the second holder 256 is coupled to a second pivotable member 264 and configured to pivot about a second axis BX. A first actuator 258 may be coupled to the proximal end of the first pivotable member 262 and the elongated body 252 to adjust a height of the first holder 254 and a second actuator 260 may be coupled to the second pivotable member 264 to adjust a height of the second holder 256. The first and second actuators 258, 260 may be supported by the elongated body 252. To rotate the pivotable members 262, 264 relative to the elongated body 252.

Figure 33:
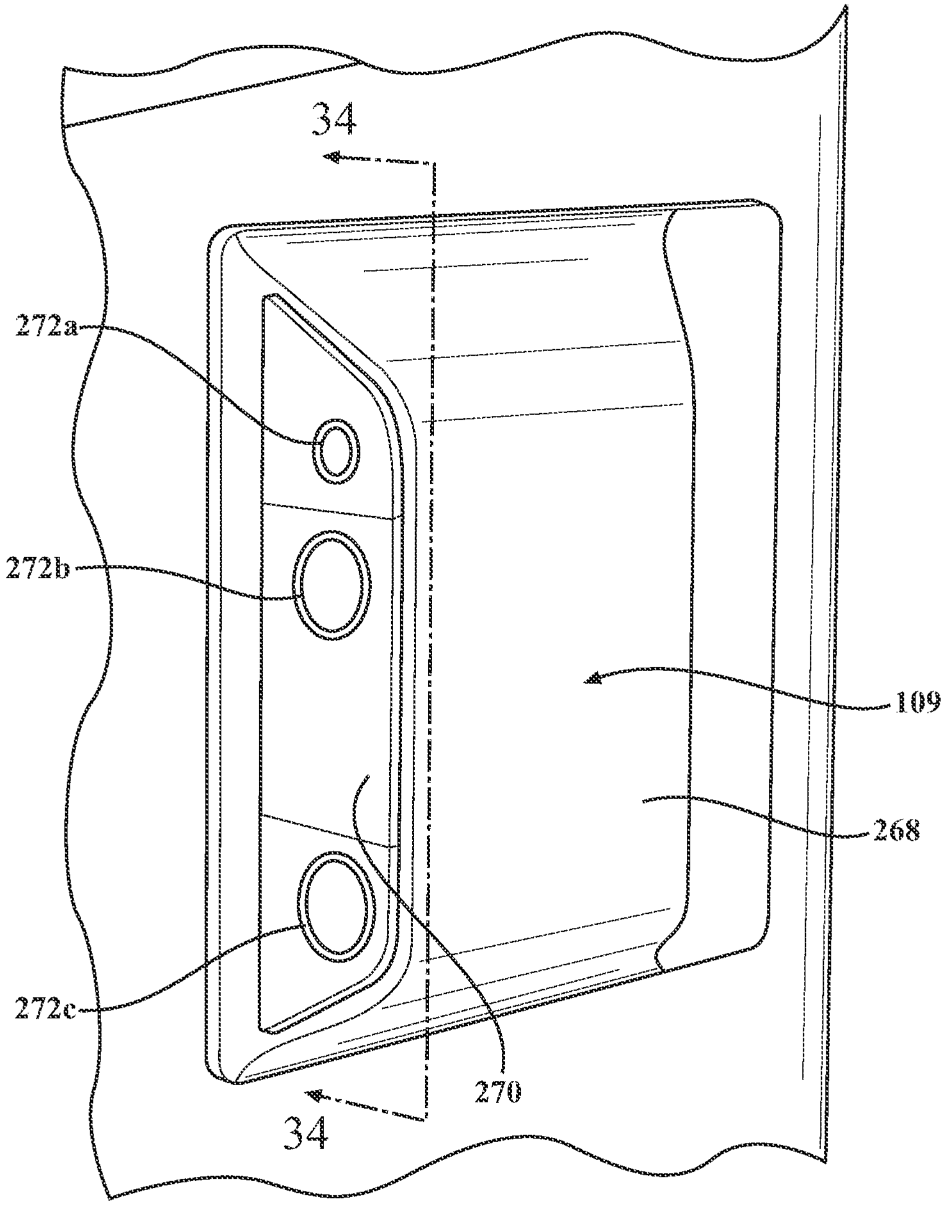
FIG. 33 is a partial perspective view of a smoke evacuation unit of the medical waste collection system.

Referring to FIG. 33, the medical waste collection system 100 may comprise the smoke evacuation subsystem or unit 109. The smoke evacuation unit 109 may be utilized for removing smoke created during a medical procedure. More specifically, the smoke evacuation unit may be configured to draw surgical smoke through an instrument to be filtered within the chassis 102 and the housing 105. However, other uses for the smoke evacuation unit 109 are evident to those skilled in the art. Suitable construction and operation of one smoke evacuation system is disclosed in commonly-owned United States Patent Publication No. 2014/0338529, published Nov. 20, 2014, the entire contents of which are hereby incorporated by reference.

Figure 34:
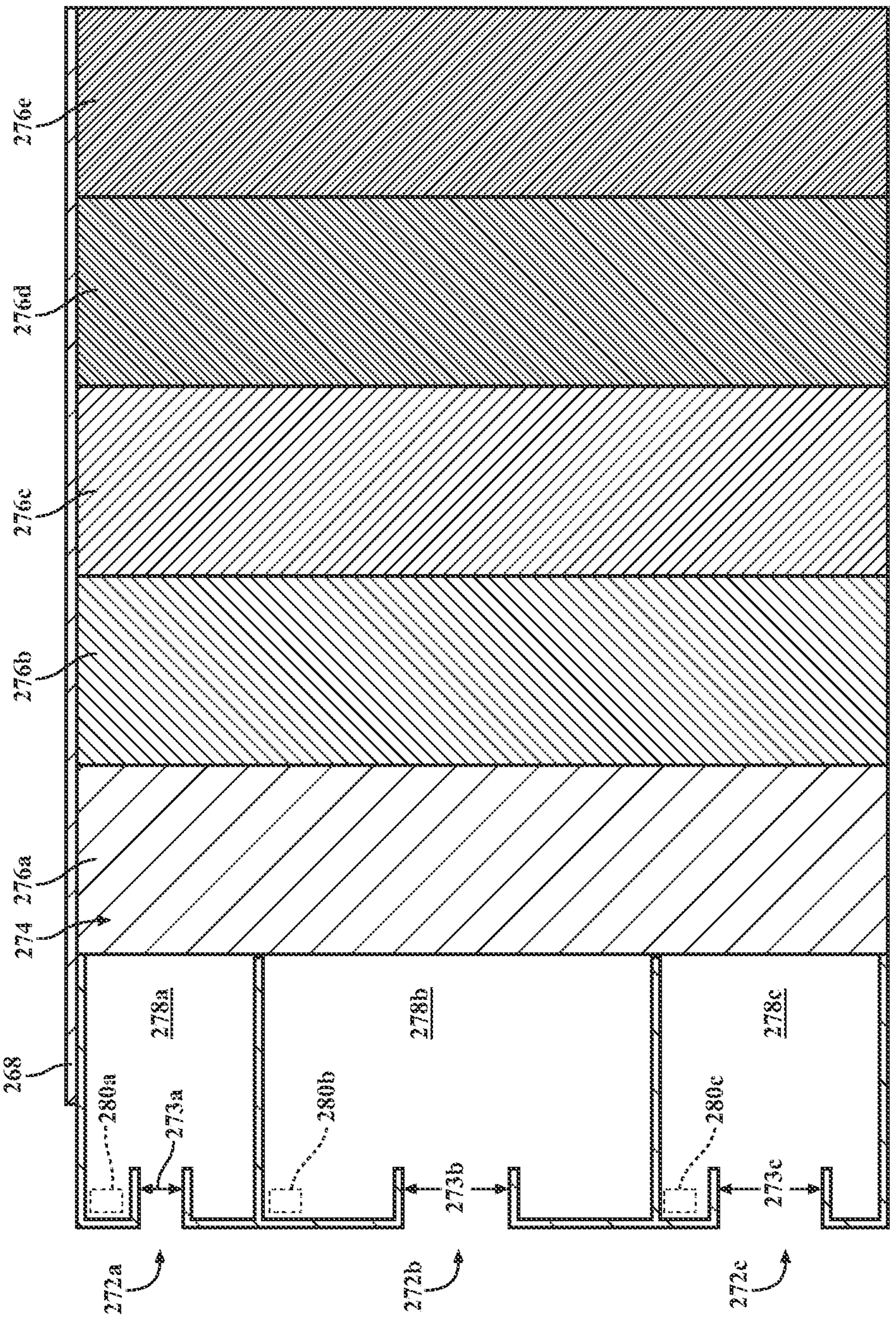
FIG. 34 is a sectional view of the smoke evacuation unit taken along line 34-34 of FIG. 33.

Referring to FIGS. 33 and 34, a perspective view of a configuration of a smoke evacuation unit 109 and a sectional view of an interior of the smoke evacuation unit 109 are illustrated, respectively. Accordingly, the smoke evacuation unit 109 may have an enclosure 268 that is integral with or coupled to the housing 105. The enclosure 268 may comprise a faceplate 270 having a front surface facing the front portion 204 of the housing 105. The faceplate 270 may define one or more ports 272*a*, 272*b*, 272*c* for receiving smoke evacuation lines (not shown) used in the medical procedure. The front surface may be oriented to extend perpendicularly from the housing 105. The ports 272*a*, 272*b*, 272*c* may face forward toward the front portion 204 of the housing 105 to facilitate easier connection of the smoke evacuation lines to the ports 272 of the smoke evacuation unit 109. The one or more ports 272*a*, 272*b*, 272*c* may be oriented in the same direction as the opening of the manifold receiver 110 such that smoke evacuation lines are introduced into ports 272*a*, 272*b*, 272*c* in the same direction as a manifold is introduced into the manifold receiver 110. The ports 272*a*, 272*b*, 272*c* may be arranged vertically with respect to gravity to maintain a low profile of the enclosure 268 relative to the housing 105. The port 272*a*, 272*b*, 272*c* may be sized differently to accommodate connections to different sized couplers/ends of smoke evacuation lines.

The smoke evacuation unit 109 may further comprise a filter portion 274 disposed within the enclosure 268. The filter portion 274 of the enclosure 268 may comprise one or more filter layers 276A, 276B, 276C, 276D, 276E. Each of the filter layers 276A, 276B, 276C, 276D, 276E may comprise differing materials and/or pore sizes configured to collect different sizes and/or types of particulates as liquids or gases pass through the various filter layers 276A, 276B, 276C, 276D, 276E.

The smoke evacuation unit 109 may further include a liquid trap 278*a* 278*b*, 278*c*, for each port 272*a*, 272*b*, 272*c* disposed between the ports 272*a*, 272*b*, 272*c* and the filter portion. The liquid trap 278*a* 278*b*, 278*c* may comprise an absorbent material to prevent fluid from entering the filter portion 274. Alternatively, the liquid trap 278*a* 278*b*, 278*c* may be a void of sufficient size to permit the liquid to descend to a sump prior to encountering the filter portion 274. The smoke evacuation unit 109 may further comprise a smoke sensor 280 disposed within the enclosure 268. The smoke sensor 280 may comprise an optical sensor, a chemical sensor, or a laser sensor. For example, an optical sensor may comprise an infrared emitting diode (IRED) and an phototransistor are diagonally arranged such that the optical sensor may detect the reflected light of dust in air. In some configurations, the smoke sensor 280 may be disposed between the liquid trap 278*a* 278*b*, 278*c* and the filter portion 274, such that the smoke sensor 280 is responsive to smoke received from the smoke evacuation lines that has already passed through the liquid trap 278*a* 278*b*, 278*c*.

In another configuration, the smoke evacuation unit 109 may comprise a power sensor (not shown) that generates a power signal responsive to power being supplied to a surgical instrument (e.g., an electrocautery device). The power signal may be received by the controller 113 to operate suction on the smoke evacuation unit 109. In one example, the controller 113 may receive the power signal from the power sensor and increase suction in the smoke evacuation unit 109. In some configurations, the smoke evacuation unit 109 may comprise a projection extending away from the enclosure 268, such as a clip or hook, for supporting a smoke evacuation line. The power sensor may be supported by the clip or the enclosure 268 adjacent the projection for generating a power signal responsive to power being supplied to the surgical instrument through the smoke evacuation line while the smoke evacuation line is supported by the projection.

Figure 26:
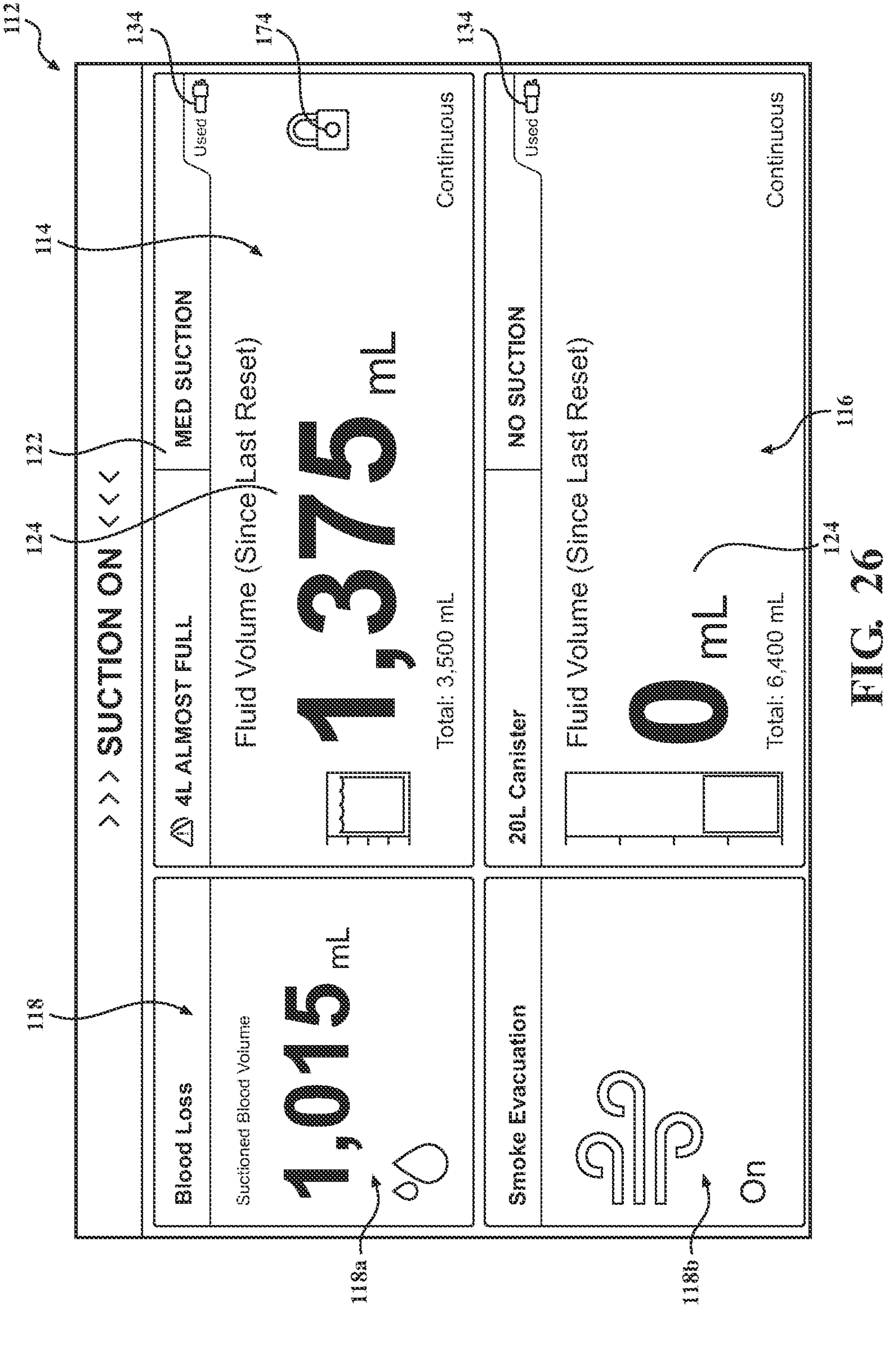
FIG. 26 illustrates a twenty-third exemplary configuration of the user interface for the medical waste collection system.

Several implementations have been discussed in the foregoing description. However, the implementations discussed herein are not intended to be exhaustive or limit the invention to any particular form. Modifications and variations are possible in light of the above teachings and may be practiced otherwise than as specifically described. For example, FIG. 26 shows another implementation in which the working tile 118 is divided into a first working tile 118*a* and a second working tile 118*b*. Particularly if more than two features of the medical waste collection system 100 are concurrently operating, the first and second working tiles 118*a*, 118*b* may provide such information. The presence of multiple working tiles also permits the text to be displayed larger, along with larger icons that may be more instantly recognizable to the user. The toolbar 120 and/or the vacuum meter 128 may be provided on the user interface 112 shown in FIG. 26.

The present disclosure also comprises the following clauses, with specific features laid out in dependent clauses, that may specifically be implemented as described in greater detail with reference to the configurations and drawings above.

I. A medical waste collection system for collecting waste material, the medical waste collection system comprising: a waste canister; a vacuum source configured to provide a vacuum on the waste canister; a chassis for supporting the waste canister and the vacuum source; and a support pole assembly coupled to the chassis, the support pole assembly comprising, an elongated body extending from the chassis, the elongated body comprising a first telescoping portion and a second telescoping portion, the second telescoping portion slidably moveable relative to the first telescoping portion, a first holder coupled to the first telescoping portion and disposed at a first elevation, and a second holder coupled to the second telescoping portion and moveable with the second telescoping portion relative to the first holder to at least a second elevation different from the first elevation, and an actuator coupled to the chassis and the second telescoping portion to move the second telescoping portion and the second holder relative to the first holder.

II. A medical waste collection system for collecting waste material, the medical waste collection system comprising: a waste canister; a vacuum source configured to provide a vacuum on the waste canister; a chassis for supporting the waste canister and the vacuum source; and a support pole assembly coupled to the chassis, the support pole assembly comprising, an elongated body extending from the chassis, a pivotable member having a proximal end pivotably coupled to the elongated body and a distal end disposed opposite the proximal end, a first holder coupled to the elongated body and disposed at a first elevation, and a second holder coupled to the distal end of the pivotable member and moveable with the distal end of the pivotable member relative to the elongated body and the first holder to at least a second elevation different from the first elevation, and an actuator coupled to the elongated body and the proximal end of the pivotable member to pivot pivotable member and move the second holder relative to the elongated body.

III. The medical waste collection system of clause I or II, wherein at least one of the first and second holders comprises one holder selected from a group consisting of a hook, a clamp, and a projection.

IV. A medical waste collection system for collecting waste material, the medical waste collection system comprising: a waste canister; a vacuum source configured to provide a vacuum on the waste canister; a housing at least partially surrounding the waste canister, the housing defining an opening for permitting a user to view the waste canister through the housing; a cover assembly coupled to the housing, the cover assembly comprising, a cover moveable between a first position where the cover occludes the opening and a second position where the cover at least partially does not occlude the opening, and a sensor coupled to one of the housing and the cover and configured to generate a signal responsive to movement of the cover from the first position to the second position; a light source assembly disposed within the housing adjacent the waste canister, the light source assembly comprising a light source configured to illuminate the waste canister; and a controller coupled to the sensor and the light source assembly, the controller configured to receive the signal from the sensor and to operate the light source of the light assembly to illuminate the waste canister responsive to the cover moving from the first position to the second position.

V. A medical waste collection system for collecting waste material, the medical waste collection system comprising: a waste canister; a vacuum source configured to provide a vacuum on the waste canister; a housing; and a smoke evacuation unit comprising, an enclosure coupled to the housing and extending outwardly away from the housing, and a faceplate having a front surface that extends perpendicularly from the housing, the faceplate defining one or more ports in the front surface for receiving smoke evacuation lines.

VI. The medical waste collection system of clause V, further comprising a manifold receiver coupled to the housing and defining an opening oriented to receive a manifold, wherein the one or more ports of the faceplate are each oriented in the same direction as the opening of the manifold receiver such that smoke evacuation lines are introduced into the one or more ports in the same direction as a manifold is introduced into the manifold receiver.

VII. The medical waste collection system of clause V or VI, wherein at least two of the one or more ports are arranged vertically with respect to gravity.

VIII. The medical waste collection system of any one of clauses V-VII, wherein at least one port of the one or more ports is sized differently from another port of the one or more ports.

The invention claimed is:

1. A method of operating a medical waste collection system including a waste canister, a vacuum source, a user interface, and a controller, the method comprising:

receiving, at the user interface, a first input from a user indicative of a suction limit;

controlling, with the controller, operation of the vacuum source such that an actual vacuum level generated by the vacuum source does not exceed the suction limit;

receiving, at the user interface, a second input from the user to activate a suction limit lock at a selected vacuum level;

permitting, with the controller, adjustment of the suction limit below the selected vacuum level while the suction limit lock is engaged, wherein the controller is configured to operate the vacuum source to adjust the actual vacuum level based on the adjustment of the suction limit;

preventing, with the controller, adjustment of the suction limit above the selected vacuum level associated with the suction limit lock;

receiving, at the user interface, a third input from the user indicative of an attempt to adjust the suction limit above the selected vacuum level associated with the suction limit lock;

determining, with the controller, a trigger condition based on the third user input; and displaying, on the user interface, a prompt with an option to disable the suction limit lock based on the trigger condition.

2. The method of claim 1, wherein the user interface includes a rotatable knob, and wherein the method further comprises:

receiving, at the user interface, the third input by rotation of the rotatable knob;

wherein determining the trigger condition comprises determining, with the controller, a desired rate of increase of the suction limit based on a speed with which the rotatable knob is rotated; and displaying, on the user interface, the prompt if the trigger condition exceeds a predetermined threshold.

3. The method of claim 1, wherein the user interface includes a rotatable knob, and wherein the method further comprises:

receiving, at the user interface, the third input by rotation of the rotatable knob;

receiving, at the user interface, at least one additional input by a separate, further rotation of the rotatable knob that are indicative of additional attempt to adjust the suction limit above the selected vacuum level;

wherein determining the trigger condition comprises determining, with the controller, a quantity of additional attempts; and displaying, on the user interface, the prompt if the trigger condition exceeds a predetermined threshold.

4. The method of claim 1, further comprising:

receiving, at the user interface, a fourth input from the user to the prompt, wherein the controller is configured to deactivate the suction limit lock in response to the fourth input;

receiving the third input from the user, wherein the adjustment of the suction limit above the selected vacuum level is permitted; and operating the vacuum source to adjust the actual vacuum level based on the adjustment of the suction limit.

5. The method of claim 1, wherein the medical waste collection system includes memory storing data indicative of a maximum suction level associated with a respective one of predetermined clinical procedures, wherein the method further comprises:

receiving, at the user interface, a selection of one of the predetermined clinical procedures; and automatically activating the suction limit lock and setting the selected vacuum level to be equal to the maximum suction level associated with the selected one of the predetermined clinical procedures.

6. The method of claim 1, further comprising displaying, on the user interface, a graphical representation of an operating range of the vacuum source, a visual marking overlying or adjacent the graphical representation that is indicative of the suction limit, and an indicia near the graphical representation that is indicative of the suction limit lock being activated.

7. The method of claim 6, wherein the graphical representation is arcuate vacuum meter including colored zones representative of low suction, medium suction, and high suction.

8. The method of claim 7, wherein the indicia of the suction limit lock is a padlock icon positioned on a concave side of the arcuate vacuum meter.

9. A method of operating a medical waste collection system including a waste canister, a vacuum source, a user interface, and a controller, the method comprising:

receiving, at the user interface, a first input from a user indicative of a suction limit;

controlling, with the controller, operation of the vacuum source such that an actual vacuum level generated by the vacuum source does not exceed the suction limit;

receiving, at the user interface, a second input from the user to activate a suction limit lock at a selected vacuum level;

permitting, with the controller, adjustment of the suction limit below the selected vacuum level while the suction limit lock is engaged, wherein the controller is configured to operate the vacuum source to adjust the actual vacuum level based on the adjustment of the suction limit;

receiving, at the user interface, a third input from the user indicative of an attempt to adjust the suction limit above the selected vacuum level associated with the suction limit lock;

determining, with the controller, a trigger condition based on the third user input; and displaying, on the user interface, a prompt with an option to disable the suction limit lock based on the trigger condition.

10. The method of claim 9, wherein the user interface includes a rotatable knob, and wherein the method further comprises:

receiving, at the user interface, the third input by rotation of the rotatable knob;

wherein determining the trigger condition comprises determining, with the controller, a desired rate of increase of the suction limit based on a speed with which the rotatable knob is rotated, and displaying, on the user interface, the prompt if the trigger condition exceeds a predetermined threshold.

11. The method of claim 9, wherein the user interface includes a rotatable knob, and wherein the method further comprises:

receiving, at the user interface, the third input by rotation of the rotatable knob;

receiving, at the user interface, at least one additional input by a separate, further rotation of the rotatable knob that are indicative of additional attempt to adjust the suction limit above the selected vacuum level;

wherein determining the trigger condition comprises determining, with the controller, a quantity of additional attempts; and displaying, on the user interface, the prompt if the trigger condition exceeds a predetermined threshold.

12. The method of claim 9, further comprising:

receiving, at the user interface, a fourth input from the user to the prompt, wherein the controller is configured to deactivate the suction limit lock in response to the fourth input;

receiving the third input from the user, wherein the adjustment of the suction limit above the selected vacuum level is permitted; and operating the vacuum source to adjust the actual vacuum level based on the adjustment of the suction limit.

13. The method of claim 9, wherein the medical waste collection system includes memory storing data indicative of a maximum suction level associated with a respective one of predetermined clinical procedures, wherein the method further comprises:

receiving, at the user interface, a selection of one of the predetermined clinical procedures; and automatically activating the suction limit lock and setting the selected vacuum level to be equal to the maximum suction level associated with the selected one of the predetermined clinical procedures.

14. The method of claim 9, further comprising displaying, on the user interface, a vacuum meter of an operating range of the vacuum source, a visual marking overlying the vacuum meter that is indicative of the suction limit, and an indicia near the vacuum meter that is indicative of the suction limit lock being activated.

* * * * *